(12) United States Patent
Ghosh

(10) Patent No.: US 12,280,260 B2
(45) Date of Patent: Apr. 22, 2025

(54) EVALUATION AND ADJUSTMENT OF LEFT BUNDLE BRANCH (LBB) PACING THERAPY

(71) Applicant: Medtronic, Inc., Minneapolis, MN (US)

(72) Inventor: Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 686 days.

(21) Appl. No.: 17/521,277

(22) Filed: Nov. 8, 2021

(65) Prior Publication Data

US 2022/0168576 A1 Jun. 2, 2022

Related U.S. Application Data

(60) Provisional application No. 63/120,460, filed on Dec. 2, 2020.

(51) Int. Cl.
*A61N 1/372* (2006.01)
*A61N 1/37* (2006.01)

(52) U.S. Cl.
CPC .......... *A61N 1/371* (2013.01); *A61N 1/3702* (2013.01)

(58) Field of Classification Search
CPC ...... A61N 1/371; A61N 1/3702; A61N 1/365; A61N 1/3682; A61N 1/3756; A61B 5/271; A61B 5/282; A61B 5/303; A61B 5/308; A61B 5/327; A61B 5/33; A61B 5/36; A61B 5/366; A61B 5/367; A61B 5/4848

See application file for complete search history.

(56) References Cited

U.S. PATENT DOCUMENTS

| | | | |
|---|---|---|---|
| 3,672,353 A | 6/1972 | Crovella et al. |
| 4,233,987 A | 11/1980 | Feingold |
| 4,374,382 A | 2/1983 | Markowitz |
| 4,402,323 A | 9/1983 | White |
| 4,428,378 A | 1/1984 | Anderson et al. |
| 4,497,326 A | 2/1985 | Curry |
| 4,530,204 A | 7/1985 | Mortara |
| 4,566,456 A | 1/1986 | Koning et al. |
| 4,593,702 A | 6/1986 | Kepski |
| 4,624,265 A | 11/1986 | Grassi |

(Continued)

FOREIGN PATENT DOCUMENTS

| | | |
|---|---|---|
| CN | 1043621 A | 7/1990 |
| CN | 1253761 A | 5/2000 |

(Continued)

OTHER PUBLICATIONS

International Search Report and Written Opinion for PCT/US2021/061333, mailed Mar. 21, 2022; 18 Pages.

(Continued)

*Primary Examiner* — Eugene T Wu
(74) *Attorney, Agent, or Firm* — Mueting Raasch Group

(57) ABSTRACT

Systems and methods are described herein related to the evaluation and adjustment of left bundle branch (LBB) pacing therapy. Evaluation of the LBB pacing therapy may utilize electrical activity monitored from a plurality of external electrodes. The electrical activity may be used to provided one or more metrics of dispersion of surrogate cardiac electrical activation times, which may then be used to evaluate, and potentially adjust the LBB pacing therapy.

29 Claims, 9 Drawing Sheets

(56) References Cited

U.S. PATENT DOCUMENTS

| | | |
|---|---|---|
| 4,674,511 A | 6/1987 | Cartmell |
| 4,763,660 A | 8/1988 | Kroll et al. |
| 4,777,955 A | 10/1988 | Brayten et al. |
| 4,787,389 A | 11/1988 | Tarjan |
| 4,979,507 A | 12/1990 | Heinz et al. |
| 4,979,598 A | 12/1990 | John |
| 5,052,388 A | 10/1991 | Sivula et al. |
| 5,054,496 A | 10/1991 | Wen et al. |
| 5,117,824 A | 6/1992 | Keimel et al. |
| 5,174,286 A | 12/1992 | Chirife |
| 5,311,873 A | 5/1994 | Savard et al. |
| 5,331,960 A | 7/1994 | Lavine |
| 5,334,220 A | 8/1994 | Sholder |
| 5,443,492 A | 8/1995 | Stokes et al. |
| 5,485,849 A | 1/1996 | Panescu et al. |
| 5,514,163 A | 5/1996 | Markowitz et al. |
| 5,545,186 A | 8/1996 | Olsen et al. |
| 5,552,645 A | 9/1996 | Weng |
| 5,628,778 A | 5/1997 | Kruse et al. |
| 5,671,752 A | 9/1997 | Sinderby et al. |
| 5,683,429 A | 11/1997 | Mehra |
| 5,683,432 A | 11/1997 | Goedeke et al. |
| 5,687,737 A | 11/1997 | Branham et al. |
| 5,728,140 A | 3/1998 | Salo et al. |
| 5,755,736 A | 5/1998 | Gillberg et al. |
| 5,800,467 A | 9/1998 | Park et al. |
| 5,810,740 A | 9/1998 | Paisner |
| 5,876,336 A | 3/1999 | Swanson et al. |
| 5,891,045 A | 4/1999 | Albrecht et al. |
| 5,922,014 A | 7/1999 | Warman et al. |
| 5,964,795 A | 10/1999 | McVenes et al. |
| 6,055,448 A | 4/2000 | Anderson et al. |
| 6,115,628 A | 9/2000 | Stadler et al. |
| 6,128,535 A | 10/2000 | Maarse et al. |
| 6,141,588 A | 10/2000 | Cox et al. |
| 6,187,032 B1 | 2/2001 | Ohyu et al. |
| 6,205,357 B1 | 3/2001 | Ideker et al. |
| 6,226,542 B1 | 5/2001 | Reisfeld |
| 6,236,883 B1 | 5/2001 | Ciaccio et al. |
| 6,243,603 B1 | 6/2001 | Ideker et al. |
| 6,246,898 B1 | 6/2001 | Vesely et al. |
| 6,301,496 B1 | 10/2001 | Reisfeld |
| 6,311,089 B1 | 10/2001 | Mann et al. |
| 6,330,476 B1 | 12/2001 | Ben-Haim et al. |
| 6,358,214 B1 | 3/2002 | Tereschouk |
| 6,377,856 B1 | 4/2002 | Carson |
| 6,381,493 B1 | 4/2002 | Stadler et al. |
| 6,393,316 B1 | 5/2002 | Gillberg et al. |
| 6,418,346 B1 | 7/2002 | Nelson et al. |
| 6,442,433 B1 | 8/2002 | Linberg |
| 6,456,867 B2 | 9/2002 | Reisfeld |
| 6,473,638 B2 | 10/2002 | Ferek-Petric |
| 6,480,745 B2 | 11/2002 | Nelson et al. |
| 6,484,118 B1 | 11/2002 | Govari |
| 6,507,756 B1 | 1/2003 | Heynen et al. |
| 6,532,379 B2 | 3/2003 | Stratbucker |
| 6,556,866 B2 | 4/2003 | Dal Molin et al. |
| 6,584,343 B1 | 6/2003 | Ransbury et al. |
| 6,599,250 B2 | 7/2003 | Webb et al. |
| 6,609,027 B2 | 8/2003 | Kroll et al. |
| 6,625,482 B1 | 9/2003 | Panescu et al. |
| 6,640,136 B1 | 10/2003 | Helland et al. |
| 6,650,927 B1 | 11/2003 | Keidar |
| 6,711,443 B2 | 3/2004 | Osypka |
| 6,718,206 B2 | 4/2004 | Casvant |
| 6,738,674 B2 | 5/2004 | Osypka |
| 6,766,189 B2 | 7/2004 | Yu et al. |
| 6,768,923 B2 | 7/2004 | Ding et al. |
| 6,772,004 B2 | 8/2004 | Rudy |
| 6,804,555 B2 | 10/2004 | Warkentin |
| 6,847,836 B1 | 1/2005 | Sujdak |
| 6,856,830 B2 | 2/2005 | He |
| 6,882,882 B2 | 4/2005 | Struble et al. |
| 6,885,889 B2 | 4/2005 | Chinchoy |
| 6,915,149 B2 | 7/2005 | Ben-Haim |
| 6,968,237 B2 | 11/2005 | Doan et al. |
| 6,975,900 B2 | 12/2005 | Rudy et al. |
| 6,978,184 B1 | 12/2005 | Marcus et al. |
| 6,980,675 B2 | 12/2005 | Evron et al. |
| 6,988,007 B1 | 1/2006 | Morgan et al. |
| 7,016,719 B2 | 3/2006 | Rudy et al. |
| 7,031,777 B2 | 4/2006 | Hine et al. |
| 7,033,350 B2 | 4/2006 | Bahk et al. |
| 7,058,443 B2 | 6/2006 | Struble |
| 7,062,315 B2 | 6/2006 | Koyrakh et al. |
| 7,092,759 B2 | 8/2006 | Nehls et al. |
| 7,142,922 B2 | 11/2006 | Spinelli et al. |
| 7,177,704 B2 | 2/2007 | Laske et al. |
| 7,184,835 B2 | 2/2007 | Kramer et al. |
| 7,191,015 B2 | 3/2007 | Lamson et al. |
| 7,215,998 B2 | 5/2007 | Wesselink et al. |
| 7,238,158 B2 | 7/2007 | Abend |
| 7,286,866 B2 | 10/2007 | Okerlund et al. |
| 7,308,297 B2 | 12/2007 | Reddy et al. |
| 7,308,299 B2 | 12/2007 | Burrell et al. |
| 7,313,444 B2 | 12/2007 | Pianca et al. |
| 7,321,677 B2 | 1/2008 | Evron et al. |
| 7,346,381 B2 | 3/2008 | Okerlund et al. |
| 7,386,351 B2 | 6/2008 | Hine et al. |
| 7,398,116 B2 | 7/2008 | Edwards |
| 7,426,412 B1 | 9/2008 | Schecter |
| 7,454,248 B2 | 11/2008 | Burrell et al. |
| 7,499,743 B2 | 3/2009 | Vass et al. |
| 7,509,170 B2 | 3/2009 | Zhang et al. |
| 7,565,190 B2 | 7/2009 | Okerlund et al. |
| 7,587,074 B2 | 9/2009 | Zarkh et al. |
| 7,599,730 B2 | 10/2009 | Hunter et al. |
| 7,610,088 B2 | 10/2009 | Chinchoy |
| 7,613,500 B2 | 11/2009 | Vass et al. |
| 7,616,993 B2 | 11/2009 | Müssig et al. |
| 7,647,124 B2 | 1/2010 | Williams |
| 7,664,550 B2 | 2/2010 | Eick et al. |
| 7,684,863 B2 | 3/2010 | Parikh et al. |
| 7,702,390 B1 | 4/2010 | Min |
| 7,729,782 B2 | 6/2010 | William et al. |
| 7,738,954 B1 | 6/2010 | Kroll et al. |
| 7,742,629 B2 | 6/2010 | Zarkh et al. |
| 7,747,047 B2 | 6/2010 | Okerlund et al. |
| 7,751,882 B1 | 7/2010 | Helland et al. |
| 7,769,451 B2 | 8/2010 | Yang et al. |
| 7,778,685 B2 | 8/2010 | Evron et al. |
| 7,778,686 B2 | 8/2010 | Vass et al. |
| 7,787,951 B1 | 8/2010 | Min |
| 7,792,580 B2 | 9/2010 | Borowitz et al. |
| 7,801,624 B1 | 9/2010 | Flannery et al. |
| 7,813,785 B2 | 10/2010 | Okerlund et al. |
| 7,815,577 B2 | 10/2010 | Krishnan |
| 7,818,040 B2 | 10/2010 | Spear et al. |
| 7,848,807 B2 | 12/2010 | Wang |
| 7,860,580 B2 | 12/2010 | Falk et al. |
| 7,894,889 B2 | 2/2011 | Zhang |
| 7,912,544 B1 | 3/2011 | Min et al. |
| 7,917,214 B1 | 3/2011 | Gill et al. |
| 7,941,205 B2 | 5/2011 | Jung et al. |
| 7,941,213 B2 | 5/2011 | Markowitz et al. |
| 7,953,475 B2 | 5/2011 | Harlev et al. |
| 7,953,482 B2 | 5/2011 | Hess |
| 7,983,743 B2 | 7/2011 | Rudy et al. |
| 7,996,063 B2 | 8/2011 | Vass et al. |
| 7,996,070 B2 | 8/2011 | van Dam et al. |
| 8,010,191 B2 | 8/2011 | Zhu et al. |
| 8,010,194 B2 | 8/2011 | Muller |
| 8,013,133 B2 | 9/2011 | Sharma et al. |
| 8,019,402 B1 | 9/2011 | Kryzpow et al. |
| 8,019,409 B2 | 9/2011 | Rosenberg et al. |
| 8,032,229 B2 | 10/2011 | Gerber et al. |
| 8,036,743 B2 | 10/2011 | Savage et al. |
| 8,060,185 B2 | 11/2011 | Hunter et al. |
| 8,075,486 B2 | 12/2011 | Tal |
| 8,078,287 B2 | 12/2011 | Liu et al. |
| 8,112,160 B2 | 2/2012 | Foster |
| 8,150,513 B2 | 4/2012 | Chinchoy |
| 8,160,700 B1 | 4/2012 | Ryu et al. |
| 8,175,703 B2 | 5/2012 | Dong et al. |

(56) References Cited

U.S. PATENT DOCUMENTS

| | | |
|---|---|---|
| 8,180,428 B2 | 5/2012 | Kaiser et al. |
| 8,195,292 B2 | 6/2012 | Rosenberg et al. |
| 8,213,693 B1 | 7/2012 | Li |
| 8,214,041 B2 | 7/2012 | Van Gelder et al. |
| 8,265,736 B2 | 9/2012 | Sathaye et al. |
| 8,265,738 B1 | 9/2012 | Min et al. |
| 8,285,377 B2 | 10/2012 | Rosenberg et al. |
| 8,295,943 B2 | 10/2012 | Eggen et al. |
| 8,321,014 B2 | 11/2012 | Maskara et al. |
| 8,326,419 B2 | 12/2012 | Rosenberg et al. |
| 8,332,030 B2 | 12/2012 | Hess et al. |
| 8,380,308 B2 | 2/2013 | Rosenberg et al. |
| 8,401,616 B2 | 3/2013 | Verard et al. |
| 8,406,899 B2 | 3/2013 | Reddy et al. |
| 8,478,388 B2 | 7/2013 | Nguyen et al. |
| 8,509,896 B2 | 8/2013 | Doerr et al. |
| 8,527,051 B1 | 9/2013 | Hedberg et al. |
| 8,560,068 B2 | 10/2013 | Forslund |
| 8,565,880 B2 | 10/2013 | Dong et al. |
| 8,583,230 B2 | 11/2013 | Ryu et al. |
| 8,588,907 B2 | 11/2013 | Arcot-krishnamurthy et al. |
| 8,606,369 B2 | 12/2013 | Williams et al. |
| 8,615,298 B2 | 12/2013 | Ghosh et al. |
| 8,617,082 B2 | 12/2013 | Zhang et al. |
| 8,620,433 B2 | 12/2013 | Ghosh et al. |
| 8,639,333 B2 | 1/2014 | Stadler et al. |
| 8,688,234 B2 | 4/2014 | Ortega et al. |
| 8,694,099 B2 | 4/2014 | Ghosh et al. |
| 8,731,632 B1 | 5/2014 | Zarkh et al. |
| 8,738,132 B1 | 5/2014 | Ghosh et al. |
| 8,744,576 B2 | 6/2014 | Munsterman et al. |
| 8,750,998 B1 | 6/2014 | Ghosh et al. |
| 8,761,880 B2 | 6/2014 | Maskara et al. |
| 8,768,465 B2 | 7/2014 | Ghosh et al. |
| 8,805,504 B2 | 8/2014 | Sweeney |
| 8,834,384 B2 | 9/2014 | Krishnan |
| 8,861,830 B2 | 10/2014 | Brada et al. |
| 8,874,237 B2 | 10/2014 | Schilling et al. |
| 8,929,984 B2 | 1/2015 | Ghosh et al. |
| 8,942,805 B2 | 1/2015 | Shuros et al. |
| 8,948,869 B2 | 2/2015 | Ghosh et al. |
| 8,954,147 B2 | 2/2015 | Arcot-krishnamurthy et al. |
| 8,965,489 B2 | 2/2015 | Ghosh |
| 8,972,228 B2 | 3/2015 | Ghosh et al. |
| 9,002,454 B2 | 4/2015 | Ghosh et al. |
| 9,031,642 B2 | 5/2015 | Ghosh |
| 9,037,238 B2 | 5/2015 | Stadler et al. |
| 9,060,699 B2 | 6/2015 | Nearing et al. |
| 9,101,281 B2 | 8/2015 | Reinert et al. |
| 9,119,959 B2 | 9/2015 | Rys et al. |
| 9,155,897 B2 | 10/2015 | Ghosh et al. |
| 9,162,066 B2 | 10/2015 | Hedberg et al. |
| 9,168,382 B2 | 10/2015 | Shuros et al. |
| 9,199,087 B2 | 12/2015 | Stadler et al. |
| 9,215,987 B2 | 12/2015 | Trayanova et al. |
| 9,265,951 B2 | 2/2016 | Sweeney |
| 9,265,954 B2 | 2/2016 | Ghosh |
| 9,265,955 B2 | 2/2016 | Ghosh |
| 9,272,148 B2 | 3/2016 | Ghosh |
| 9,278,219 B2 | 3/2016 | Ghosh |
| 9,278,220 B2 | 3/2016 | Ghosh |
| 9,278,229 B1 | 3/2016 | Reinke et al. |
| 9,282,907 B2 | 3/2016 | Ghosh |
| 9,320,446 B2 | 4/2016 | Gillberg et al. |
| 9,381,362 B2 | 7/2016 | Ghosh et al. |
| 9,474,457 B2 | 10/2016 | Ghosh et al. |
| 9,486,151 B2 | 11/2016 | Ghosh et al. |
| 9,510,763 B2 | 12/2016 | Ghosh et al. |
| 9,526,435 B2 | 12/2016 | Ghosh |
| 9,550,058 B2 | 1/2017 | Foster |
| 9,586,050 B2 | 3/2017 | Ghosh et al. |
| 9,586,052 B2 | 3/2017 | Gillberg et al. |
| 9,591,982 B2 | 3/2017 | Ghosh et al. |
| 9,603,651 B2 | 3/2017 | Ghosh |
| 9,610,045 B2 | 4/2017 | Du et al. |
| 9,675,579 B2 | 6/2017 | Grubac et al. |
| 9,700,728 B2 | 7/2017 | Ghosh |
| 9,737,223 B2 | 8/2017 | Du et al. |
| 9,750,941 B2 | 9/2017 | Ghosh |
| 9,757,567 B2 | 9/2017 | Ghosh et al. |
| 9,764,143 B2 | 9/2017 | Ghosh et al. |
| 9,776,009 B2 | 10/2017 | Ghosh et al. |
| 9,782,094 B2 | 10/2017 | Du et al. |
| 9,789,319 B2 | 10/2017 | Sambelashvil |
| 9,962,097 B2 | 5/2018 | Ghosh et al. |
| 9,974,457 B2 | 5/2018 | Ghosh et al. |
| 10,022,060 B2 | 7/2018 | Nearing et al. |
| 10,123,745 B1 | 11/2018 | Katra et al. |
| 10,154,794 B2 | 12/2018 | Stadler et al. |
| 10,206,601 B2 | 2/2019 | Gillberg et al. |
| 10,251,555 B2 | 4/2019 | Ghosh et al. |
| 10,780,279 B2 | 9/2020 | Ghosh |
| 10,850,107 B2 | 12/2020 | Li et al. |
| 10,850,108 B2 | 12/2020 | Li et al. |
| 2002/0072682 A1 | 6/2002 | Hopman et al. |
| 2002/0087089 A1 | 7/2002 | Ben-Haim |
| 2002/0143264 A1 | 10/2002 | Ding et al. |
| 2002/0161307 A1 | 10/2002 | Yu et al. |
| 2002/0169484 A1 | 11/2002 | Mathis et al. |
| 2003/0018277 A1 | 1/2003 | He |
| 2003/0023295 A1 | 1/2003 | Osypka et al. |
| 2003/0023296 A1 | 1/2003 | Osypka et al. |
| 2003/0050670 A1 | 3/2003 | Spinelli et al. |
| 2003/0105495 A1 | 6/2003 | Yu et al. |
| 2003/0199938 A1 | 10/2003 | Smits et al. |
| 2003/0199956 A1 | 10/2003 | Struble et al. |
| 2003/0236466 A1 | 12/2003 | Tarjan et al. |
| 2004/0010201 A1 | 1/2004 | Korzinov et al. |
| 2004/0015081 A1 | 1/2004 | Kramer et al. |
| 2004/0054388 A1 | 3/2004 | Osypka |
| 2004/0059237 A1 | 3/2004 | Narayan et al. |
| 2004/0097806 A1 | 5/2004 | Hunter et al. |
| 2004/0102812 A1 | 5/2004 | Yonce et al. |
| 2004/0122479 A1 | 6/2004 | Spinelli et al. |
| 2004/0153127 A1 | 8/2004 | Gordon et al. |
| 2004/0162496 A1 | 8/2004 | Yu et al. |
| 2004/0172078 A1 | 9/2004 | Chinchoy |
| 2004/0172079 A1 | 9/2004 | Chinchoy |
| 2004/0193223 A1 | 9/2004 | Kramer et al. |
| 2004/0215245 A1 | 10/2004 | Stahmann et al. |
| 2004/0215252 A1 | 10/2004 | Verbeek et al. |
| 2004/0220635 A1 | 11/2004 | Burnes |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0090870 A1 | 4/2005 | Hine et al. |
| 2005/0096522 A1 | 5/2005 | Reddy et al. |
| 2005/0107839 A1 | 5/2005 | Sanders |
| 2005/0109339 A1 | 5/2005 | Stahmann et al. |
| 2005/0149138 A1 | 7/2005 | Min et al. |
| 2005/0197674 A1 | 9/2005 | McCabe et al. |
| 2005/0216068 A1 | 9/2005 | Lee et al. |
| 2006/0074285 A1 | 4/2006 | Zarkh et al. |
| 2006/0095107 A1 | 5/2006 | Osypka |
| 2006/0206153 A1 | 9/2006 | Libbus et al. |
| 2006/0224198 A1 | 10/2006 | Dong et al. |
| 2006/0235478 A1 | 10/2006 | Van Gelder et al. |
| 2006/0253162 A1 | 11/2006 | Zhang et al. |
| 2007/0016261 A1 | 1/2007 | Dong et al. |
| 2007/0078490 A1 | 4/2007 | Cowan et al. |
| 2007/0142871 A1 | 6/2007 | Libbus et al. |
| 2007/0167809 A1 | 7/2007 | Dala-Krishna |
| 2007/0232943 A1 | 10/2007 | Harel et al. |
| 2007/0250129 A1 | 10/2007 | Van Oort |
| 2007/0265508 A1 | 11/2007 | Sheikhzadeh-Nadjar et al. |
| 2008/0021336 A1 | 1/2008 | Dobak et al. |
| 2008/0058656 A1 | 3/2008 | Costello et al. |
| 2008/0082136 A1 | 4/2008 | Gaudiani |
| 2008/0119903 A1 | 5/2008 | Arcot-Krishnamurthy et al. |
| 2008/0140143 A1 | 6/2008 | Ettori et al. |
| 2008/0146954 A1 | 6/2008 | Bojovic et al. |
| 2008/0177344 A1 | 7/2008 | Maskara et al. |
| 2008/0242976 A1 | 10/2008 | Robertson et al. |
| 2008/0249585 A1 | 10/2008 | Lippert et al. |

(56) References Cited

U.S. PATENT DOCUMENTS

| | | |
|---|---|---|
| 2008/0269818 A1 | 10/2008 | Sullivan et al. |
| 2008/0269823 A1 | 10/2008 | Burues et al. |
| 2008/0281195 A1 | 11/2008 | Heimdal |
| 2008/0288008 A1 | 11/2008 | Lee |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0043352 A1 | 2/2009 | Brooke et al. |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0084382 A1 | 4/2009 | Jalde et al. |
| 2009/0093857 A1 | 4/2009 | Markowitz et al. |
| 2009/0099468 A1 | 4/2009 | Thiagalingam et al. |
| 2009/0099469 A1 | 4/2009 | Flores |
| 2009/0099619 A1 | 4/2009 | Lessmeier et al. |
| 2009/0112109 A1 | 4/2009 | Kuklik et al. |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0177344 A1 | 7/2009 | James et al. |
| 2009/0198298 A1 | 8/2009 | Kaiser et al. |
| 2009/0216112 A1 | 8/2009 | Assis et al. |
| 2009/0232448 A1 | 9/2009 | Barmash et al. |
| 2009/0234414 A1 | 9/2009 | Sambelashvili et al. |
| 2009/0254140 A1 | 10/2009 | Rosenberg et al. |
| 2009/0270729 A1 | 10/2009 | Corbucci et al. |
| 2009/0270937 A1 | 10/2009 | Yonce et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |
| 2010/0016917 A1 | 1/2010 | Efimov et al. |
| 2010/0022873 A1 | 1/2010 | Hunter et al. |
| 2010/0049063 A1 | 2/2010 | Dobak, III |
| 2010/0069983 A1 | 3/2010 | Peacock et al. |
| 2010/0069987 A1 | 3/2010 | Min et al. |
| 2010/0087888 A1 | 4/2010 | Maskara |
| 2010/0094149 A1 | 4/2010 | Kohut et al. |
| 2010/0113954 A1 | 5/2010 | Zhou |
| 2010/0114229 A1 | 5/2010 | Chinchoy |
| 2010/0121403 A1 | 5/2010 | Schecter et al. |
| 2010/0145405 A1 | 6/2010 | Min et al. |
| 2010/0174137 A1 | 7/2010 | Shim |
| 2010/0191131 A1 | 7/2010 | Revishvili et al. |
| 2010/0198292 A1 | 8/2010 | Honeck et al. |
| 2010/0228138 A1 | 9/2010 | Chen |
| 2010/0234916 A1 | 9/2010 | Turcott et al. |
| 2010/0249622 A1 | 9/2010 | Olson |
| 2010/0254583 A1 | 10/2010 | Chan et al. |
| 2010/0268059 A1 | 10/2010 | Ryu et al. |
| 2011/0004111 A1 | 1/2011 | Gill et al. |
| 2011/0004264 A1 | 1/2011 | Siejko et al. |
| 2011/0009918 A1 | 1/2011 | Bornzin |
| 2011/0014510 A1 | 1/2011 | Miyashisa et al. |
| 2011/0022112 A1 | 1/2011 | Min |
| 2011/0054286 A1 | 3/2011 | Crosby |
| 2011/0054559 A1 | 3/2011 | Rosenberg et al. |
| 2011/0054560 A1 | 3/2011 | Rosenberg et al. |
| 2011/0075896 A1 | 3/2011 | Matsumoto |
| 2011/0092809 A1 | 4/2011 | Nguyen et al. |
| 2011/0112398 A1 | 5/2011 | Zarkh et al. |
| 2011/0118803 A1 | 5/2011 | Hou et al. |
| 2011/0137369 A1 | 6/2011 | Ryu et al. |
| 2011/0144510 A1 | 6/2011 | Ryu et al. |
| 2011/0172728 A1 | 7/2011 | Wang |
| 2011/0184297 A1 | 7/2011 | Vitali et al. |
| 2011/0190615 A1 | 8/2011 | Phillips et al. |
| 2011/0201915 A1 | 8/2011 | Gogin et al. |
| 2011/0213260 A1 | 9/2011 | Keel et al. |
| 2011/0264158 A1 | 10/2011 | Dong et al. |
| 2011/0319954 A1 | 12/2011 | Niazi et al. |
| 2011/0319956 A1 | 12/2011 | Zhu et al. |
| 2012/0004567 A1 | 1/2012 | Eberle et al. |
| 2012/0101539 A1 | 4/2012 | Zhu et al. |
| 2012/0101542 A1 | 4/2012 | Arcot-Krishnamurthy et al. |
| 2012/0101543 A1 | 4/2012 | Demmer et al. |
| 2012/0101546 A1 | 4/2012 | Stadler et al. |
| 2012/0109244 A1 | 5/2012 | Anderson et al. |
| 2012/0158089 A1 | 6/2012 | Bocek et al. |
| 2012/0179056 A1 | 7/2012 | Moulder et al. |
| 2012/0203090 A1 | 8/2012 | Min |
| 2012/0253419 A1 | 10/2012 | Rosenberg et al. |
| 2012/0283587 A1 | 11/2012 | Ghosh et al. |
| 2012/0284003 A1 | 11/2012 | Ghosh et al. |
| 2012/0296387 A1 | 11/2012 | Zhang et al. |
| 2012/0296388 A1 | 11/2012 | Zhang et al. |
| 2012/0302904 A1 | 11/2012 | Lian et al. |
| 2012/0303084 A1 | 11/2012 | Kleckner et al. |
| 2012/0310101 A1 | 12/2012 | Patantgay et al. |
| 2012/0310297 A1 | 12/2012 | Sweeney |
| 2012/0330179 A1 | 12/2012 | Yuk et al. |
| 2013/0006332 A1 | 1/2013 | Sommer et al. |
| 2013/0018250 A1 | 1/2013 | Caprio et al. |
| 2013/0018251 A1 | 1/2013 | Caprio et al. |
| 2013/0030491 A1 | 1/2013 | Stadler et al. |
| 2013/0060298 A1 | 3/2013 | Splett et al. |
| 2013/0072790 A1 | 3/2013 | Ludwig et al. |
| 2013/0079861 A1 | 3/2013 | Reinert et al. |
| 2013/0090701 A1 | 4/2013 | Liu et al. |
| 2013/0096446 A1 | 4/2013 | Michael et al. |
| 2013/0116739 A1 | 5/2013 | Brada et al. |
| 2013/0131529 A1 | 5/2013 | Jia et al. |
| 2013/0131749 A1 | 5/2013 | Sheldon et al. |
| 2013/0131751 A1 | 5/2013 | Stadler et al. |
| 2013/0136035 A1 | 5/2013 | Bange et al. |
| 2013/0150913 A1 | 6/2013 | Bornzin et al. |
| 2013/0158621 A1 | 6/2013 | Ding et al. |
| 2013/0165983 A1 | 6/2013 | Ghosh et al. |
| 2013/0165988 A1 | 6/2013 | Ghosh |
| 2013/0184697 A1 | 7/2013 | Han et al. |
| 2013/0261471 A1 | 10/2013 | Saha et al. |
| 2013/0261688 A1 | 10/2013 | Dong et al. |
| 2013/0289640 A1 | 10/2013 | Zhang et al. |
| 2013/0296726 A1 | 11/2013 | Niebauer et al. |
| 2013/0304407 A1 | 11/2013 | George et al. |
| 2013/0324828 A1 | 12/2013 | Nishiwaki et al. |
| 2013/0325078 A1 | 12/2013 | Whiting et al. |
| 2014/0005563 A1 | 1/2014 | Ramanathan et al. |
| 2014/0018872 A1 | 1/2014 | Siejko et al. |
| 2014/0018892 A1 | 1/2014 | Dahlberg |
| 2014/0046389 A1 | 2/2014 | Anderson et al. |
| 2014/0107507 A1 | 4/2014 | Ghosh et al. |
| 2014/0107723 A1 | 4/2014 | Hou et al. |
| 2014/0107724 A1 | 4/2014 | Shuros et al. |
| 2014/0135866 A1 | 5/2014 | Ramanathan et al. |
| 2014/0135867 A1 | 5/2014 | Demmer et al. |
| 2014/0163633 A1 | 6/2014 | Ghosh et al. |
| 2014/0222099 A1 | 8/2014 | Sweeney |
| 2014/0236252 A1 | 8/2014 | Ghosh et al. |
| 2014/0276125 A1 | 9/2014 | Hou et al. |
| 2014/0277233 A1 | 9/2014 | Ghosh |
| 2014/0277239 A1 | 9/2014 | Maskara et al. |
| 2014/0323882 A1 | 10/2014 | Ghosh et al. |
| 2014/0323892 A1 | 10/2014 | Ghosh et al. |
| 2014/0323893 A1 | 10/2014 | Ghosh et al. |
| 2014/0371807 A1 | 12/2014 | Ghosh et al. |
| 2014/0371808 A1 | 12/2014 | Ghosh et al. |
| 2014/0371832 A1 | 12/2014 | Ghosh et al. |
| 2014/0371833 A1 | 12/2014 | Ghosh et al. |
| 2015/0032016 A1 | 1/2015 | Ghosh |
| 2015/0032171 A1 | 1/2015 | Ghosh |
| 2015/0032172 A1 | 1/2015 | Ghosh |
| 2015/0032173 A1 | 1/2015 | Ghosh |
| 2015/0045811 A1 | 2/2015 | Schilling |
| 2015/0045849 A1 | 2/2015 | Ghosh et al. |
| 2015/0142069 A1 | 5/2015 | Sambelashvili |
| 2015/0157225 A1 | 6/2015 | Gillberg et al. |
| 2015/0157231 A1 | 6/2015 | Gillberg et al. |
| 2015/0157232 A1 | 6/2015 | Gillberg et al. |
| 2015/0157865 A1 | 6/2015 | Gillberg et al. |
| 2015/0216434 A1 | 8/2015 | Ghosh et al. |

(56) References Cited

U.S. PATENT DOCUMENTS

| | | |
|---|---|---|
| 2015/0217110 A1 | 8/2015 | Ollivier |
| 2015/0265840 A1 | 9/2015 | Ghosh et al. |
| 2016/0022164 A1 | 1/2016 | Brockway et al. |
| 2016/0030747 A1 | 2/2016 | Thakur et al. |
| 2016/0030751 A1 | 2/2016 | Ghosh et al. |
| 2016/0045737 A1 | 2/2016 | Ghosh et al. |
| 2016/0045738 A1 | 2/2016 | Ghosh et al. |
| 2016/0045744 A1 | 2/2016 | Gillberg et al. |
| 2016/0059002 A1 | 3/2016 | Grubac et al. |
| 2016/0184590 A1 | 6/2016 | Ghosh |
| 2016/0213928 A1 | 7/2016 | Ghosh |
| 2016/0220142 A1 | 8/2016 | Gillberg et al. |
| 2016/0271393 A1 | 9/2016 | Yu et al. |
| 2016/0317840 A1 | 11/2016 | Stadler et al. |
| 2016/0339248 A1 | 11/2016 | Schrock et al. |
| 2017/0001011 A1 | 1/2017 | An et al. |
| 2017/0028205 A1 | 2/2017 | Ghosh |
| 2017/0049347 A1 | 2/2017 | Ghosh et al. |
| 2017/0071675 A1 | 3/2017 | Dawoud et al. |
| 2017/0246460 A1 | 8/2017 | Ghosh |
| 2017/0246461 A1 | 8/2017 | Ghosh |
| 2017/0303840 A1 | 10/2017 | Steckler et al. |
| 2017/0304624 A1 | 10/2017 | Friedman et al. |
| 2017/0340887 A1 | 11/2017 | Engels et al. |
| 2018/0020938 A1 | 1/2018 | Du et al. |
| 2018/0140847 A1 | 5/2018 | Taff et al. |
| 2018/0199843 A1 | 7/2018 | Ghosh et al. |
| 2018/0250514 A1 | 9/2018 | Ghosh |
| 2018/0256904 A1 | 9/2018 | Li et al. |
| 2018/0263522 A1 | 9/2018 | Ghosh et al. |
| 2018/0264258 A1 | 9/2018 | Cheng et al. |
| 2018/0326215 A1 | 11/2018 | Ghosh |
| 2019/0022378 A1 | 1/2019 | Prillinger et al. |
| 2019/0030331 A1 | 1/2019 | Ghosh et al. |
| 2019/0111264 A1 | 4/2019 | Zhou |
| 2019/0111265 A1 | 4/2019 | Zhou |
| 2019/0111270 A1 | 4/2019 | Zhou |
| 2019/0126040 A1 | 5/2019 | Shuros et al. |
| 2019/0126049 A1 | 5/2019 | Casavant et al. |
| 2019/0126050 A1 | 5/2019 | Shuros et al. |
| 2019/0134404 A1 | 5/2019 | Sheldon et al. |
| 2019/0134405 A1 | 5/2019 | Sheldon et al. |
| 2019/0143117 A1 | 5/2019 | Ghosh |
| 2019/0160288 A1 | 5/2019 | Stegemann et al. |
| 2019/0183370 A1 | 6/2019 | Gillberg et al. |
| 2019/0192023 A1 | 6/2019 | Ghosh |
| 2019/0192092 A1 | 6/2019 | Habn et al. |
| 2019/0192860 A1 | 6/2019 | Ghosh et al. |
| 2019/0201698 A1 | 7/2019 | Herrmann et al. |
| 2019/0217097 A1 | 7/2019 | Thakur et al. |
| 2019/0261876 A1 | 8/2019 | Ghosh et al. |
| 2019/0269926 A1 | 9/2019 | Ghosh |
| 2019/0275329 A1 | 9/2019 | Brisben et al. |
| 2019/0290905 A1 | 9/2019 | Yang et al. |
| 2019/0290909 A1* | 9/2019 | Ghosh ............... A61N 1/3625 |
| 2019/0298903 A1 | 10/2019 | Gillberg et al. |
| 2020/0069949 A1 | 3/2020 | Ghosh |
| 2020/0261725 A1 | 8/2020 | Yang et al. |
| 2020/0261734 A1 | 8/2020 | Yang et al. |
| 2020/0352470 A1 | 11/2020 | Ghosh |
| 2021/0023367 A1 | 1/2021 | Ghosh |
| 2021/0085986 A1 | 3/2021 | Li et al. |
| 2021/0106245 A1 | 4/2021 | Ghosh |
| 2021/0106337 A1 | 4/2021 | Ghosh |
| 2021/0106832 A1 | 4/2021 | Ghosh |
| 2021/0128925 A1 | 5/2021 | Ghosh |
| 2021/0236038 A1 | 8/2021 | Hoglund et al. |

FOREIGN PATENT DOCUMENTS

| | | |
|---|---|---|
| CN | 1878595 A | 12/2006 |
| CN | 101073502 A | 11/2007 |
| EP | 1072284 A2 | 1/2001 |
| EP | 1234597 A2 | 8/2002 |
| EP | 1504713 | 2/2005 |
| EP | 2016976 | 1/2009 |
| EP | 2391270 | 7/2011 |
| EP | 1925337 | 3/2012 |
| EP | 2436309 A2 | 4/2012 |
| EP | 2435132 | 8/2013 |
| WO | WO 1998/026712 | 6/1998 |
| WO | WO 1999/006112 | 2/1999 |
| WO | WO 2000/045700 | 8/2000 |
| WO | WO 2001/067950 | 9/2001 |
| WO | WO 2003/005900 | 1/2003 |
| WO | WO 2003/070323 | 8/2003 |
| WO | WO 2005/056108 A2 | 6/2005 |
| WO | WO 2006/069215 A2 | 6/2006 |
| WO | WO 2006/105474 A2 | 10/2006 |
| WO | WO 2006/115777 | 11/2006 |
| WO | WO 2006/117773 | 11/2006 |
| WO | WO 2007/013994 A2 | 2/2007 |
| WO | WO 2007/027940 A2 | 3/2007 |
| WO | WO 2007/013994 A3 | 4/2007 |
| WO | WO 2007/027940 A3 | 6/2007 |
| WO | WO 2007/139456 | 12/2007 |
| WO | WO 2008/151077 A2 | 12/2008 |
| WO | WO 2006/069215 A3 | 6/2009 |
| WO | WO 2009/079344 | 6/2009 |
| WO | WO 2009/139911 A2 | 11/2009 |
| WO | WO 2009/148429 | 12/2009 |
| WO | WO 2010/019494 | 2/2010 |
| WO | WO 2010/071520 | 6/2010 |
| WO | WO 2010/071849 A2 | 6/2010 |
| WO | WO 2010/088040 | 8/2010 |
| WO | WO 2010/088485 | 8/2010 |
| WO | WO 2011/070166 | 6/2011 |
| WO | WO 2011/090622 | 7/2011 |
| WO | WO 2011/099992 | 8/2011 |
| WO | WO 2012/037471 A2 | 3/2012 |
| WO | WO 2012/037471 A3 | 6/2012 |
| WO | WO 2012/106297 A2 | 8/2012 |
| WO | WO 2012/109618 A2 | 8/2012 |
| WO | WO 2012/110940 | 8/2012 |
| WO | WO 2012/109618 A3 | 11/2012 |
| WO | WO 2012/151364 | 11/2012 |
| WO | WO 2012/151389 | 11/2012 |
| WO | WO 2013/006724 A2 | 1/2013 |
| WO | WO 2013/010165 | 1/2013 |
| WO | WO 2013/010184 | 1/2013 |
| WO | WO 2013/006724 | 4/2013 |
| WO | WO 2014/055692 A2 | 4/2014 |
| WO | WO 2014/179454 | 11/2014 |
| WO | WO 2014/179459 A2 | 11/2014 |
| WO | WO 2014/179459 A3 | 1/2015 |
| WO | WO 2015/013271 | 1/2015 |
| WO | WO 2015/013493 | 1/2015 |
| WO | WO 2015/013574 | 1/2015 |
| WO | WO 2017/192892 A2 | 11/2017 |
| WO | WO 2019/173599 | 9/2019 |
| WO | WO 2020/058314 | 3/2020 |
| WO | WO 2021/123271 | 6/2021 |

OTHER PUBLICATIONS

Zhang Shu et al., "Left Bundle Branch Pacing JACC Review Topic of the Week" J Amer College Cardiol, Elsevier, Amsterdam NL. Dec. 9, 2019; 74(24): 3039-49.
U.S. Appl. No. 61/819,946, filed May 6, 2013.
U.S. Appl. No. 17/361,721, filed Jun. 29, 2021.
U.S. Appl. No. 17/385,259, filed Jul. 26, 2021.
International Search Report and Written Opinion issued May 3, 2012 for International Application No. PCT/US2012/036302; 9 pages.
International Search Report and Written Opinion issued Sep. 3, 2012 for International Application No. PCT/US2012/036262 9 pages.
International Search Report and Written Opinion issued Aug. 6, 2014 for International Application No. PCT/US2014/036153; 14 pages.
International Search Report and Written Opinion issued Nov. 7, 2014 for International Application No. PCT/US2014/036163; 12 pages.

(56) References Cited

OTHER PUBLICATIONS

International Search Report and Written Opinion issued Oct. 24, 2014 for International Application No. PCT/US2014/041929; 14 pages.
International Search Report and Written Opinion issued Oct. 28, 2014 for International Application No. PCT/US2014/041928; 15 pages.
International Search Report and Written Opinion issued on Nov. 4, 2014 for International Application No. PCT/US2014/0247583; 7 pages.
International Search Report and Written Opinion issued on Nov. 12, 2014 for International Application No. PCT/US2014/047971; 7 pages.
International Search Report and Written Opinion issued on Nov. 12, 2014 for International Application No. PCT/US2014/048120; 7 pages.
International Search Report and Written Opinion issued on Mar. 9, 2015 for International Application No. PCT/US2014/069214; 11 pages.
International Search Report and Written Opinion issued Mar. 16, 2015 for International Application No. PCT/US2014/069182; 11 pages.
International Search Report and Written Opinion issued Mar. 17, 2015 for International Application No. PCT/US2014/069192; 11 pages.
International Search Report and Written Opinion issued on Apr. 8, 2015 for International Application No. PCT/US2014/069070; 11 pages.
International Search Report and Written Opinion issued on Jun. 11, 2015 for International Application No. PCT/US2015/021442; 13 pages.
International Search Report and Written Opinion for PCT/US2018/056295, mailed Dec. 19, 2018, 18 pages.
International Search Report and Written Opinion for PCT/US2018/056257, mailed Jan. 3, 2019, 16 pages.
International Search Report and Written Opinion for PCT/US2018/056292, mailed Jan. 30, 2019, 16 pages.
International Search Report and Written Opinion for PCT/US2018/056242, mailed Feb. 11, 2019, 16 pages.
International Search Report and Written Opinion issued May 27, 2019 for International Application No. PCT/US2019/023549; 15 pages.
International Preliminary Report on Patentability for PCT/US2018/056242, mailed Apr. 30, 2020, 9 pages.
International Preliminary Report on Patentability for PCT/US2018/056257, mailed Apr. 30, 2020, 9 pages.
International Preliminary Report on Patentability for PCT/US2018/056292, mailed Apr. 30, 2020, 9 pages.
International Preliminary Report on Patentability for PCT/US2018/056295, mailed Apr. 30, 2020, 9 pages.
International Search Report and Written Opinion for PCT Application No. PCT/US2020/016468 dated May 7, 2020, 10 pages.
International Search Report and Written Opinion for PCT Application No. PCT/US2020/016369 dated May 26, 2020, 10 pages.
International Search Report and Written Opinion issued Jun. 4, 2020 for International Application No. PCT/US2020/019589; 11 pages.
International Search Report and Written Opinion from PCT Application No. PCT/US2020/053474 dated Jan. 13, 2021, 8 pages.
International Search Report and Written Opinion from PCT Application No. PCT/US2020/053472 dated Jan. 12, 2021, 8 pages.
International Search Report and Written Opinion from PCT Application No. PCT/US2020/058627 dated Jan. 28, 2021, 9 pages.
International Search Report and Written Opinion from PCT Application No. PCT/US2020/053794 dated Feb. 15, 2021, 11 pages.
International Search Report and Written Opinion from PCT Application No. PCT/US2021/033046 dated Aug. 9, 2021, 16 pages.
Abdelrahman et al., "Clinical Outcomes of His Bundle Pacing Compared to Right Ventricular Pacing," *J Am Coll Cardiol.*, May 22, 2018; 71(20):2319-2330.

Ahmed et al., "Right Ventricular Apical Pacing-induced Left Ventricular Dyssynchrony is Associated with a Subsequent Decline in Ejection Fraction," *Heart Rhythm*, Apr. 2014; 11(4):602-608.
Ajijola et al., "Permanent His-bundle pacing for cardiac resynchronization therapy: Initial feasibility study in lieu of left ventricular lead," *Heart Rhythm*, Sep. 2017; 14(9):1353-1361.
Al-Hesayen et al., "Adverse effects of atrioventricular synchronous right ventricular pacing on left ventricular sympathetic activity, efficiency, and hemodynamic status," *Am J Physiol Heart Circ Physiol.*, 2006; 291(5):H2377-H2379.
Anderson et al., "Wilhelm His Junior and his bundle," *J Electrocardiol.*, 2016; 49:637-643.
Aquilina, "A Brief History of Cardiac Pacing", Images Paediatr Cardiol. 8 (2), Apr.-Jun. 2006, 117 pages.
Babu et al., "Three-dimensional echocardiography with left ventricular strain analyses helps earlier prediction of right ventricular pacing-induced cardiomyopathy," *J Saudi Heart Assoc.*, Apr. 2018;30(2):102-107.
Barba-Pichardo et al., "Permanent His-Bundle Pacing in patients with Infra-Hisian Atrioventricular Block," *Revista Espanola de Cardiologia*, Jun. 2006; 59(6):553-558.
Biffi et al., "Occurrence of Phrenic Nerve Stimulation in Cardiac Resynchronization Therapy Patients: the Role of Left Ventricular Lead Type and Placement Site," *Europace*, 2013; 15:77-82.
Bortolotto et al., "Pre-implantation interlead EKG heterogeneity is superior to QRS complex duration in predicting mechanical super-response and survival in patients receiving cardiac resynchronization therapy", *Heart Rhythm*, Mar. 10, 2020, 35 pages.
Botker MD, PhD., et al., "Electromechanical Mapping for Detection of Myocardial Viability in Patients with ischemia Cardiomyopathy," Circulation, Mar. 2001; vol. 103, No. 12, pp.
Cantù et al., "Validation of Criteria for Selective His Bundle and Para-Hisian Permanent Pacing," *Pacing & Clinical Electrophysiology*, Dec. 2006; 29(12):1326-1333.
"CardioGuide System Enables Real-Time Navigation of Left Ventricular Leads During Medtronic CRT Implants," Press Release, Apr. 9, 2013, Medtronic, Inc., 2 pgs.
Catanzari et al., "Permanent His-Bundle Pacing Maintains Long-Term Ventricular Synchrony and Left Ventricular Performance, Unlike Conventional Right Ventricular Apical Pacing," *EP Europace*, Apr. 2013; 15(4):546-553.
Chang et al., "Tricuspid Valve Dysfunction Following Pacemaker of Cardioverter-Defibrillator Implantation," *J Am Coll Cardiol.*, May 9, 2017; 69(18): 2331-2341.
Cho et al., Cerclage parahisian septal pacing through the septal perforator branch of the great cardiac vein: Bedside-to-bench development of a novel technique and lead, *Heart Rhythm Society*, Dec. 2019;16(12):1834-1840.
Chon et al., "TCT-18: Novel Concept of Catheter-Based Treatment for Tricuspid Regurgitation(Cerclage-TR block)," Pusan National University Yangsan Hospital, Yangsan, South Korea NHLBI, NIH, USA* Sep. 21, 2018.
Choy et al., "Right ventricular pacing impairs endothelial function in man." *Europace*, Jun. 2011; 13(6):853-858.
Cuculich, P.S., et al., "The Electrophysiological Cardiac Ventricular Substrate in Patients After Myocardial Infection" J. Am. Coll. Cardiol. 2011; 58:1893-1902.
Czerwinska et al., "Method of Segmentation of Thorax Organs Images Applied to Modeling the Cardiac Electrical Field." *Engineering in Medicine and Biology Society*, Proceedings of the 22$^{nd}$ Annual International Conference of the IEEE, vol. 1, 23, Jul. 23, 2000.; pp. 402-405.
Dandamudi et al., "My Approach to Choosing Ventricular Pacing Sites in Patients With Severe Heart Failure," *J Cardio Electrophysiol.*, Jul. 2011; 22(7):813-817.
Dandamudi et al., "How to perform permanent His bundle pacing in routine clinical practice," *Heart Rhythm Society*, Jun. 2016; 13(6):1362-1366.
Dandamudi et al., "The Complexity of the His Bundle: Understanding Its Anatomy and Physiology through the Lens of the Past and the Present," Sep. 2016, DOI: 10.1111/pace.12925.

(56) References Cited

OTHER PUBLICATIONS

Dawoud, F. et al., "Inverse Electrocardiogramaging to Assess Electrical Dyssynchrony in Cardiac Resynchronization Therapy Patients," Computing in Cardiology, 2012; 39:993-996.
De Sisti et al., "Adverse Effects of Long-Term Right Ventricular Apical Pacing and Identification of Patients at Risk of Atrial Fibrillation and Heart Failure," PACE, Aug. 2012; 35(8):1035-1043.
Deshmukh et al., "Permanent, Direct His-Bundle Pacing: A Novel Approach to Cardiac Pacing in Patients With Normal Hus-Purkinje Activation," *Circulation*, Feb. 29, 2000, 101(8):869-877.
Deshmukh et al., "Direct His-Bundle Pacing: Present and Future," *PACE*, Jun. 2004; 27 [6 Pt.2]:862-70.
Deshmukh et al., "Direct His-Bundle Triple Site Pacing: A Novel Alternative to Bi-Ventricular Pacing," Heart Rhythm 2009, Presentation Abstract, May 14, 2009.
Deshmukh et al., "Comparison of Direct His Bundle and Biventricular Pacing," Heart Rhythm 2009, Poster Session V, May 15, 2009.
Deshmukh et al., "His bundle pacing: Initial experience and lessons learned," *J Electrocardiol.*, 2016; 49:658-663.
Dreger et al., "Pacing-induced cardiomyopathy in patients with right ventricular stimulation for >15 years," *EP Europace*, Feb. 2012; 14(2):238-242.
El-Sherif et al., "Normalization of Bundle Branch Block Patterns by Distal His Bundle Pacing. Clinical and Experimental Evidence of Longitudinal Dissociation in the Pathologic His Bundle," *Circulation*, Mar. 1978; 57:473-83.
Freund et al., "A Decision-Theoretic Generalization of Online Learning and an Application to Boosting," *Journal of Computer and System Sciences*, 1997; 55(1):119-139.
Friedman, "Greedy Function Approximation: A Gradient Boosting Machine," *Annals of Statistics*, 2001; 29(5):1189-1232.
Friedman, "Stochastic Gradient Boosting," *Computational Statistics and Data Analysis*, 2002; 38(4):367-378.
Friedman et al., "Additive Logistic Regression: a Statistical View of Boosting," *Annals of Statistics*, 2000; 28(2):337-374.
Friedman et al., "Intermittent Capture of the Left Bundle With Permanent His Bundle Pacing: Mechanistic Insights and Implications for an Emerging Field," Aug. 1, 2016. doi: 10.1111/jce.13057.
Fröhlig et al., "His-bundle Stimulation and Alternative RV Stimulation Sites," Mar. 2008; 19(1):30-40, German.
Fung et al., Chapter 20, Optimization of Cardiac Resynchronization Therapy, Cardiac Resynchronization Therapy, Second Edition, Copyright 2008, Blackwell Publishing Ltd., pp. 356-373.
Garrote et al., "His Bundle Pacing: Great in Theory, But Difficult in Practice," Revista Española de Cardiologia, 2006; 59(6):534-6.
Ghosh et al. "Accuracy of Quadratic Versus Linear Interpolation in Noninvasive Electrocardiogramaging (ECGI)." *Annuals of Biomedical Engineering*, vol. 33, No. 9. Sep. 2005; pp. 1187-1201.
Ghosh et al., "Cardiac Memory in Patents with Wolff-Parkinson-White Syndrome: Noninvasive Imaging of Activation and Repolarization Before and After Catheter Ablation" *Circulation*, 2008; 118:907-915. Published online Aug. 12, 2008.
Ghosh et al. "Application of L1-Norm Regularization to Epicardial Potential Solution of the Inverse Electrocardiogramoblem," *Annuals of Biomedical Engineering*, vol. 37, No. 5, May 2009: pp. 902-912.
Ghosh et al., "Electrophysiological Substrate and Intraventricular LV Dyssynchrony in Non-ischemic Heart Failure Patients Undergoing Cardiac Resynchronization Therapy," *Heart rhythm : the official journal of the Heart Rhythm Society*, 2011; 8(5):692-699.
Gierula et al., "Pacing-associated left ventricular dysfunction? Think reprogramming first!" *Heart*, May 2014; 100(10):765-769.
Gierula et al., "Patients with long-term permanent pacemakers have a high prevalence of left ventricular dysfunction," *J Cardiovasc Med*, Nov. 2015; 16(11):743-750.
Gillis et al., "Atrial Fibrillation After DDDR Pacemaker Implantation," *J Cardiovasc Electrophysiol.*, Jun. 2002; 13(6):542-547.
Gold et al., "Comparison of Stimulation Sites within Left Ventricular Veins on the Acute Hemodynamic Effects of Cardiac Resynchronization Therapy" *Heart Rhythm*, Apr. 2005; 2(4):376-381.
Gula et al., "Feasibility of His Bundle Pacing as an Alternative Pacing Site: Measurement of His Refractoriness," *J Interv Card Electrophysiol.*, 2005; 12: 69-73.
Gulrajani, "The Forward and Inverse Problems of Electrocardiography," *IEEE Imagineering in Medicine and Biology*, IEEE Service Center, vol. 17, No. 5, Sep. 1, 1988; pp. 84-101, 122.
Hansen, "Regularization Tools: A Matlab Package for Analysis and Solution of Discrete III-Posed Problems," Version 4.1 for Matlab 7.3; Mar. 2008; 128 pages. Retrieved from the Internet: Jun. 19, 2014 http://www.mathworks.com/matlabcentral/fileexchange/52-regtools.
Hayashi et al., "Impact of simple electrocardiogram markers as predictors for deterioration of left ventricular function in patients with frequent right ventricular apical pacing," *Heart Vessels*, Sep. 26, 2017; 33(3):299-308.
Hayes et al., "Cardiac Resynchronization Therapy and the Relationship of Percent Biventricular Pacing to Symptoms and Survival," *Heart Rhythm*, Sep. 2011; 8(9):1469-1475.
"Heart Failure Management" datasheet [online]. Medtronic, Minneapolis, Minnesota, [Last updated on Jun. 3, 2013].Retrieved from the Internet: www.medtronic.com; 9 pages.
"His-Bundle Pacing Papers" http://www.his-pacing.org/the-list-his-bundle-pacing-papers/, 15 pages.
Hopenfeld et al., "The Effect of Conductivity on ST—Segment Epicardial Potentials Arising from Subendocardial Ischemia," Annals of Biomedical Eng., Jun. 2005; vol. 33, No. 6, pp. 751-763.
Hoyt et al., "Reversal of Left Ventricular Dysfunction with Biventricular or His-bundle Pacing Upgrade Late after A-V Nodal Ablation/block," Heart Rhythm 2008 29th Scientific Sessions.
Hoyt et al., "Hemodynamic Evaluation of Direct His-Bundle and Parahisian Pacing," Heart Rhythm 2009, Poster Session V, May 15, 2009.
Huang et al., "Benefits of Permanent His Bundle Pacing Combined With Atrioventricular Node Ablation in Atrial Fibrillation Patients With Heart Failure With Both Preserved and Reduced Left Ventricular Ejection Fraction," *J Am Heart Assoc.*, Apr. 1, 2017; 6(4). pii: e005309.
Huang et al., "Feasibility of His Bundle Pacing in Correct Left Bundle Branch Block in Heart Failure Patients," Journal of the American College of Cardiology, vol. 70, No. 16, Suppl C, 2017, GW28-e1237, 1 page.
Hurtado, "Electrical and Anatomical Modeling of the Specialized Cardiac Conduction System, A Simulation Study", Universitat Politecnica de Valenica, March 211, 96 pp.
Jia et al., "Electrocardiogramaging of Cardiac Resynchronization Therapy in Heart Failure: Observation of Variable Electrophysiologic Responses," Heart Rhythm, vol. 3, No. 3; Mar. 1, 2006, pp. 296-310.
Karpawich et al., "Septal His-Purkinje Ventricular Pacing in Canines: A New Endocardial Electrode Approach," *Pacing Clinical Electrophysiology*, 1992; 15:2011-5.
Karpawich et al., "Altered Cardiac Histology Following Apical Right Ventricular Pacing in Patients with Congenital Atrioventricular Block," *Pacing Clin Electrophysiol.*, Sep. 1999; 22(9):1372-7.
Kentta et al., "Prediction of sudden cardiac death with automated high-throughput analysis of heterogeneity in standard resting 12-lead electrocardiograms", Heart Rhythm Societ, 2016, 8 pages.
Khoo et al., "Right Ventricular Pacing as Backup to His Bundle Pacing to Minimize Battery Drain," Heart Rhythm Society, Scientific Sessions, 2013.
Kiehl et al., "Incidence and predictors of right ventricular pacing-induced cardiomyopathy in patients with complete atrioventricular block and preserved left ventricular systolic function," *Heart Rhythm*, Dec. 2016; 13(12):2272-2278.
Kim et al., "Trans-coronary sinus intraseptal para-Hisian pacing: Cerclage pacing," *Heart Rhythm*, Apr. 2016, 13(4):992-6.
Kim, "Mitral Loop Cerclage a catheter-based treatment of functional mitral regurgitation (CSTV)," JCR 2019, EuroPCR 2018.
Komreich, "Body Surface Potential Mapping of ST Segment Changes in Acute Myocardial Infarction," *Circulation*, 1993; 87: 773-782.

(56) References Cited

OTHER PUBLICATIONS

Kronborg et al., "Left Ventricular Performance during para-His Pacing in Patients with High-degree Atrioventricular Block: an acute study," *Europace*, Jun. 2014; 14(6):841-6. Epub Dec. 14, 2011.
Kronborg et al., "His or para-His Pacing Preserves Left Ventricular Function in AV Block: a Double-blind, Randomized, Crossover Study," *Europace*, Aug. 2014; 16(8): 1189-96.
Kronborg et al., "Left ventricular regional remodeling and lead position during cardiac resynchronization therapy," *Heart Rhythm*, Apr. 17, 2018; 15(10):1542-1549.
Kronborg et al., "His Bundle Pacing: Techniques and Outcomes," *Curr Cardiol Rep.*, Jul. 2016;18(8):76.
Laske et al., "Excitation of the Intrinsic Conduction System Through His and Interventricular Septal Pacing," *PACE*, Apr. 2006; 29(4):397-405.
Lederman et al., "Mitral Cerclage Annuloplasty," Cadiovascular Intervention Program at NHLBI, Update 2017.
Lindsay, "Deleterious Effects of Right Ventricular Pacing," *The New England Journal of Medicine*, Nov. 15, 2009; 361:2183-2185.
Liu et al., "Three-Dimensional Imaging of Ventricular Activation and Electrograms from Intercavitary Recordings", IEEE 2011, vol. 58, No. Apr. 2011, pp. 868-875.
Lumason™, Brochure, Bracco Diagnostocs. Oct. 2014.
Lustgarten et al., "Direct His Bundle Pacing vs. BiVentricular Pacing in CRT Patients—A Cross-over Design Comparison," *Heart Rhythm*, 2013.
Lustgarten et al., "His-Bundle vs Biventricular Pacing in Resynchronization Therapy," *Heart Rhythm*, Jul. 2015; 12(7):1548-1557.
Lustgarten et al., "Step-wise Approach to Permanent His Bundle Pacing," The Journal of Innovations in Cardiac Rhythm Management, 2016; 7:2313-2321.
Mabo et al., "A Technique For Stable His-bundle Recording and Pacing: Electrophysiological and Hemodynamic Correlates," *Pacing Clinical Electrophysiology*, 1995; 18:1894-901.
Mazza et al., "Incidence and Predictors of Heart Failure Hospitalization and Death in Permanent Pacemaker Patients: a Single-Center Experience over Medium-term Follow-up," Europace (2013) 15. 1267-1272.
Medtronic Vitatron Carelink Encore® Programmer Model 29901 Reference Manual, 2013, Medtronic, Inc., Minneapolis, MN.
Miri et al., "Applicability of body surface potential map in computerized optimization of biventricular pacing," Annals of Biomedical Engineering, vol. 38, No. 3, Mar. 2010, pp. 865-875.
Miri et al., "Comparison of the electrophysiologically based optimization methods with different pacing parameters in patient undergoing resynchronization treatment," 30th Annual International IEEE Embs Conference, Aug. 2008, pp. 1741-1744.
Miri et al., "Computerized Optimization of Biventricular Pacing Using Body Surface Potential Map," 31st Annual International Conference of the IEEE EMBS, Sep. 2009, pp. 2815-2818.
Miri et al., "Efficiency of Timing Delays and Electrode Positions in Optimization of Biventricular Pacing: A Simulation Study," IEEE Transactions on Biomedical Engineering, Nov. 2009, pp. 2573-2582.
Modre et al., "Noninvasive Myocardial Activation Time Imaging: A Novel Inverse Algorithm Applied to Clinical ECG Mapping Data" *IEEE Transactions on Biomedical Engineering*, vol. 49; No. 10, Oct. 2002; pp. 1153-1161.
Naperkowski et al., "Direct Implantation of Permanent His Bundle Pacing Lead in Patients with Complete Heart Block Without a Mapping Catheter or a Back-up Right Ventricular Lead: Feasibility and One year Follow-up," *Heart Rhythm*, Scientific Sessions, 2013.
Narula, "Longitudinal Dissociation in the His Bundle," *Circulation*, Dec. 1977; 56(6):996-1006.
Nash et al., "An Experimental-Computational Framework for Validating in-vivo ECG Inverse Algorithms," International Journal of Bioelectromagnetism, vol. 2, No. 2, Dec. 31, 2000, 9 pp.
Niazi et al., "Comparison of Lead Placement Strategies for Permanent His Bundle Pacing," Supplement, May 2011; 8(5).

Occhetta et al., "Prevention of Ventricular Desynchronization by Permanent Para- Hisian Pacing after Atrioventricular Node Ablation in Chronic Atrial Fibrillation," *Journal of the American College of Cardiology*, May 16, 2006; 47(10):1938-45.
Occhetta et al., "Future Easy and Physiological Cardiac Pacing," *Journal of Cardiology*, Jan. 26, 2011; 31(1):32-39.
Padeletti et al., "Rate Stabilization by Right Ventricular Apex or His Bundle Pacing in Patients With Atrial Fibrillation," *Europace*, 2005; 7:454-459.
Pastore et al., "Hisian area and Right Ventricular Apical Pacing Differently Affected Left Atrial Function: an Intra-patient Evaluation," *Europace*; 2013.
Pastore et al., "The Risk of Atrial Fibrillation during Right Ventricular Pacing," *Europace*, Mar. 2016; 18(3):353-8.
Potse et al., "Mathematical Modeling and Simulation of Ventricular Activation Sequences: Implications for Cardiac Resynchronization Therapy," *J. of Cardiovasc. Trans. Res.*, 2012; 5:146-158.
Prinzen et al., "Cardiac Resynchronization Therapy State-of-the-Art of Current Applications, Guidelines, Ongoing Trials, and Areas of Controversy" *Circulation*, 2013; 128: 2407-2418.
Ridgeway, "The State of Boosting," *Computing Science and Statistics*, 1999; 31:172-181.
Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010; 21(2):219-22.
Scheinman et al., "Long-term His-Bundle Pacing and Cardiac Function," *Circulation* Feb. 29, 2000; 101:836-837.
Scherlag et al., "Functional aspects of His bundle physiology and pathophysiology: Clinical implications," *J Electrocardiol.*, Jan.-Feb. 2017; 50(1)151-155.
Sharma et al., "Permanent His-bundle Pacing is Feasible, Safe, and Superior to Right Ventricular Pacing in Routine Clinical Practice," *Heart Rhythm*, Feb. 2015; 12(2):305-312.
Sharma, "His Bundle Pacing or Biventricular Pacing for Cardiac Resynchronization Therapy in Heart Failure: Discovering New Methods for an Old Problem," *J Atr Fibrillation*, Dec. 31, 2016.
Sharma et al., "Permanent His Bundle Pacing for Cardiac Resynchronization Therapy in Patients With Heart Failure and Right Bundle Branch Block," *Circ Arrhythm Electrophysiol.*, Sep. 2018;11(9):e006613.
Sharma et al., "Safety and Feasibility of Permanent His Bundle Pacing Without a Guiding Mapping Catheter or a Back-Up Right Ventricular Lead in Routine Clinical Practice", Heart Rhythm, vol. 10, No. 5, May 2013, 1 page.
Silva et al., "Cardiac Resynchronization Therapy in Pediatric Congenital Heart Disease: Insights from Noninvasive Electrocardiogramaging" *Heart Rhythm*, vol. 6, No. 8. Aug. 1, 2009; pp. 1178-1185.
Singh et al., "Left Ventricular Lead Position and Clinical Outcome in the Multicenter Automatic Defibrillator Implantation Trial-Cardiac Resynchronization Therapy (MADIT-CRT) Trial," *Circulation*, 2011; 123:1159-1166.
Sperzel et al., "Intraoperative Characterization of Interventricular Mechanical Dyssynchrony Using Electroanatomic Mapping System—A Feasibility Study," *Journal of Interventional Cardiac Electrophysiology*, Nov. 2012; 35(2):189-96.
Steinhaus BM., "Estimating cardiac transmembrane activation and recovery times from unipolar and bipolar extracellular electrograms: a simulation study," Circulation Research, 1989, 64:449-462.
Strik et al., "Electrical and Mechanical Ventricular Activation During Left Bundle Branch Block and Resynchronization," *J. of Cardiovasc. Trans. Res.*, 2012; 5:117-126.
Su et al., "Pacing and sensing optimization of permanent His-bundle pacing in cardiac resynchronization therapy/implantable cardioverter defibrillators patients: value of integrated bipolar configuration," *EP Europace*, 18(9):1399-1405.
Svendsen et al., "Computational Models of Cardiac Electrical Activation," Chapter 5, Computational Nov. 2010, pp. 73-88.
Sweeney et al., "Analysis of Ventricular Activation Using Surface Electrocardiogra Predict Left Ventricular Reverse Volumetric Remodeling During Cardiac Resynchronization Therapy," *Circulation*, Feb. 9, 2010; 121(5):626-34. Available online Jan. 25, 2010.

(56) References Cited

OTHER PUBLICATIONS

Sweeney et al., QRS Fusion Complex Analysis Using Wave Interference to Predict Reverse Remodeling During Cardiac Resynchronization Therapy, heart Rhythm, 2014, 11:806-813.
Sweeney et al., "Adverse Effect of Ventricular Pacing on Heart Failure and Atrial Fibrillation Among Patients With Normal Baseline QRS Duration in a Clinical Trial of Pacemaker Therapy for Sinus Node Dysfunction," *Circulation*, Jun. 17, 2003; 107(23):2932-2937.
Tan et al., "Interlead heterogeneit of R- and T-wave morphology in standard 12-lead ECGs predicts sustained ventricular tachycardia/fibrillation and arrhythmic death in patients with cardiomyopathy", J. Cardiovasc Electrophysiol. 2017, 28, pp. 1324-1333.
Teng et al., "Physiological mechanisms of QRS narrowing in bundle branch block patients undergoing permanent His bundle pacing," *J Electrocardiol.*, 2016; 49(5):644-648.
Teng et al., "Usefulness of His Bundle Pacing to Achieve Electrical Resynchronization in Patients With Complete Left Bundle Branch Block and the Relation Between Native QRS Axis, Duration, and Normalization," *American Journal of Cardiology*, May 28, 2016; 118(4):527-534.
Thambo et al., "Detrimental ventricular remodeling in patients with congenital complete heart block and chronic right ventricular apical pacing," *Circulation*, Dec. 21, 2004; 110(25):3766-72.
Turner et al, "Electrical and Mechanical Components of Dyssynchrony in Heart Failure Patients with Normal QRS Duration and Left Bundle-Branch Block," *Circulation* 2004; 109: 2544-2549.
Van Deursen et al., "Vectorcardiography as a Tool for Easy Optimization of Cardiac Resynchronization Therapy in Canine LBBB Hearts," *Circulation Arrhythmia and Electrophysiology*, Jun. 1, 2012; 5(3):544-52. Available online Apr. 24, 2012.
Van Deursen et al., "Vectorcardiography for Optimization of Stimulation Intervals in Cardiac Resynchronization Therapy". J. of Cardiovasc. Trans. Res., vol. 8, No. 2, Mar. 6, 2015, pp. 128-137.
Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.
Varma et al., "Placebo CRT," *Journal of Cardiovascular Electrophysiology*, vol. 19, Aug. 2008; p. 878.
Vijayaraman et al., "Permanent His Bundle Pacing in Patients with Advanced Heart Block: Single Center Experience in Unselected Patients Without Mapping Catheter or Back-Up RV Pacing Lead," Heart Rhythm Society, Scientific Sessions, 2014.
Vijayaraman et al., "Anatomical approach to permanent His bundle pacing: Optimizing His bundle capture," *J Electrocardiol.*, 2016; 49: 649-657.
Vijayaraman et al., "How to Perform Permanent His Bundle Pacing: Tips and Tricks," *Pacing Clin Electrophysiol.*, Dec. 2016; 39(12):1298-1304.
Vijayaraman et al., "The Continued Search for Physiological Pacing Where Are We Now?" *Journal of the American College of Cardiology*, Jun. 27, 2017; 69(25):3099-3114.
Vijayaraman et al., "His Bundle Injury Current during Implantation of Permanent His Bundle Pacing Lead Predicts Excellent Pacing Outcomes," Heart Rhythm Society, Scientific Sessions, 2014.
Vijayaraman et al., "Acute His-Bundle Injury Current during Permanent His-Bundle Pacing Predicts Excellent Pacing Outcomes," Pacing Clinical Electrophysiology, Jan. 14, 2015. doi: 10.1111/pace.12571.
Vijayaraman et al., "Electrophysiologic Insights Into Site of Atrioventricular Block: Lessons From Permanent His Bundle Pacing," *JACC: Clinical Electrophysiology*, Dec. 2015; 1(6):571-581.
Vijayaraman et al., "Permanent His bundle pacing: Electrophysiological and echocardiographic observations from long-term follow-up," *PACE*, Jul. 2017; 40:883-891.
Vijayaraman et al., "Permanent His Bundle Pacing (HBP): Recommendations From a Multi-Center HBP Collaborative Working Group for Standardization of Definitions, Implant Measurements and Follow-Up," Oct. 2017; DOI: http://dx.doi.org/10.1016/j.hrthm.
Vijayaraman et al., "His Bundle Pacing," *Journal of the American College of Cardiology*, Aug. 2018; 72(8).
Wang et al., "Application of the Method of Fundamental Solutions to Potential-based Inverse Electrocardiography," Annals of Biomedical Engineering, Aug. 2006, pp. 1272-1288.
Wellens, MD et al., "The Electrocardiogram 102 Years After Einthoven," Circulation, Feb. 2004; vol. 109, No. 5, pp. 562-564.
Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.
Wilson et al., "Strategically targeting calcium: Altering activation sequence to reverse remodel the failing ventricle," *Heart Rhythm*, Oct. 2018;15(10):1550-1551.
Worsnick et al., "Direct His Bundle Pacing in a Patient with Complete Heart Block Requiring Implantable Defibrillator," *The Journal of Innovation in Cardiac Rhythm Management*, Aug. 2013; 492.
Yamauchi et al., "Permanent His-Bundle Pacing After Atrioventricular Node Ablation in a Patient With Chronic Atrial Fibrillation and Mitral Regurgitation," *Circ J*, 2005; 69:510-514.
Zanon et al., "A Feasible Approach for Direct His-Bundle Pacing Using a new Steerable Catheter to Facilitate Precise Lead Placement," *JCE*, Jan. 2006; 17:29-33.
Zanon et al., "Direct His Bundle Pacing Preserves Coronary Perfusion Compared With Right Ventricular Apical Pacing: a Prospective, Cross-over Mid-term Stud," *Europace*, May 2008; 10(5):580-7.
Zanon et al., "Safety and Performance of a System Specifically Designed for Selective Site Pacing," *Pacing and Clinical Electrophysiology*, Mar. 2011; 34(3):339-347.
Zanon et al., "Direct His bundle and Parahisian Cardiac Pacing, " *A.N.E.*, Apr. 2012; 17(2):70-8.
Znojkiewicz et al., "Direct His-bundle Pacing in Patients Following AV Node Ablation," Heart Rhythm, May 2011; 8(5):Supplement.

\* cited by examiner

EVALUATION AND ADJUSTMENT OF LEFT BUNDLE BRANCH (LBB) PACING THERAPY

This application claims the benefit under 35 U.S.C. § 119 of Provisional Application No. 63/120,460, filed Dec. 2, 2020, which is incorporated herein by reference in its entirety.

The disclosure herein relates to systems and methods for use in evaluating and adjusting cardiac conduction system pacing therapy, and more specifically, left bundle branch (LBB) pacing therapy.

Implantable medical devices (IMDs), such as implantable pacemakers, cardioverters, defibrillators, or pacemaker-cardioverter-defibrillators, provide therapeutic electrical stimulation to the heart. IMDs may provide pacing to address bradycardia, or pacing or shocks in order to terminate tachyarrhythmia, such as tachycardia or fibrillation. In some cases, the medical device may sense intrinsic depolarizations of the heart, detect arrhythmia based on the intrinsic depolarizations (or absence thereof), and control delivery of electrical stimulation to the heart if arrhythmia is detected based on the intrinsic depolarizations.

IMDs may also provide cardiac resynchronization therapy (CRT), which is a form of pacing. CRT involves the delivery of pacing to the left ventricle, or both the left and right ventricles. The timing and location of the delivery of pacing pulses to the ventricle(s) may be selected to improve the coordination and efficiency of ventricular contraction.

Systems for implanting medical devices may include workstations or other equipment in addition to the implantable medical device itself. In some cases, these other pieces of equipment assist the physician or other technician with placing the intracardiac leads at particular locations on or in the heart. In some cases, the equipment provides information to the physician about the electrical activity of the heart and the location of the intracardiac lead.

SUMMARY

The illustrative systems and methods described herein may be configured to assist a user (e.g., a physician) in evaluating and adjusting cardiac conduction system pacing therapy being delivered to a patient. In particular, the illustrative systems and methods may determine, or identify, an LBB pacing location using electrical heterogeneity information (EHI) generated from electrical activity monitored by a plurality of external electrodes while delivering the LBB pacing therapy at a variety of different locations. Then, the illustrative systems and methods may determine, or identify, an atrioventricular (AV) delay for delivering the LBB pacing at using EHI generated from electrical activity monitored by the plurality of external electrodes while delivering the LBB pacing therapy at the determined LBB pacing location and at a variety of different AV delays.

In one or more embodiments, the systems and methods may be described as being noninvasive. For example, in some embodiments, the systems and methods may not need, or include, implantable devices such as leads, probes, sensors, catheters, implantable electrodes, etc. to monitor, or acquire, electrical activity (e.g., a plurality of cardiac signals) from tissue of the patient for use in evaluating and adjusting cardiac conduction system pacing therapy. Instead, the systems and methods may use electrical measurements taken noninvasively using, e.g., a plurality of external electrodes attached to the skin of a patient about the patient's torso. Additionally, it is be understood that, while the cardiac conduction system pacing therapy, and more specifically, the LBB pacing therapy, may be invasive (e.g., one or more electrodes implanted in or near the LBB of the patient's heart), the illustrative systems and methods to evaluate and adjust the invasive cardiac conduction system pacing therapy are non-invasive.

The present disclosure may be described as providing systems and methods of optimizing right ventricular dispersion by timing configuration for left bundle branch (LBB) pacing. LBB pacing may be described as an attractive solution for both brady pacing therapy and cardiac resynchronization (therapy CRT) because of better thresholds, lead stability, and ease of implant compared to His bundle pacing. However, in left bundle branch block patients, LBB pacing may generate a right bundle branch block pattern of activation, which implies still delayed or later activation of the right ventricle.

The present disclosure may utilize a plurality of external electrodes (e.g., ECG belt) to provide a surface mapping, which may be used to optimize timing of delivery of LBB pacing to maximize, and if possible, normalize conduction not only in the left ventricle but also in the right ventricle. In at least one embodiment, the illustrative systems and methods may be used to place a LBB pacing lead in a location that optimizes standard deviation of activation times (SDAT) and left ventricular dispersion based on monitored electrical activity using the plurality of external electrodes to indicate maximum global resynchronization during pacing at short atrioventricular (AV) delay (e.g., so as to avoid fusion from the right bundle branch). In at least one embodiment, a value of SDAT that is less than or equal to 20 milliseconds (ms) during LBB pacing at short AV delay and a value of left ventricular dispersion that is less than or equal to 20 ms would be indicative of engagement of the left bundle.

Once the optimal location of the LBB pacing lead is determined, the AV delay may be changed or adjusted be in steps of 20 ms and right ventricular dispersion (e.g., standard deviation of activation times in right-sided electrodes of the plurality of external electrodes) may be determined until intrinsic ventricular sensing occurs on the LBB pacing lead. Then, the AV delay that produces the minimal right ventricular dispersion while maintaining values of SDAT and left ventricular dispersion less than 20 ms may be chosen as the optimal AV delay for pacing the left bundle branch while ensuring maximum fusion from the right bundle branch.

One illustrative system may include an electrode apparatus comprising a plurality of external electrodes to be disposed proximate a patient's skin and a computing apparatus comprising processing circuitry and operably coupled to the electrode apparatus. The computing apparatus may be configured to monitor electrical activity of the patient using the plurality of external electrodes of the electrode apparatus during delivery of left bundle branch (LBB) pacing therapy, generate electrical heterogeneity information (EHI) based on the monitored electrical activity during delivery of left bundle branch (LBB) pacing therapy, determine a LBB pacing location for the LBB pacing therapy from a plurality of different LBB pacing locations based the EHI generated during the delivery of LBB pacing therapy at the plurality of different LBB pacing locations, and determine an atrioventricular (AV) delay for the LBB pacing therapy from a plurality of different AV delays based the EHI generated during the delivery of LBB pacing therapy at the identified LBB pacing location using the plurality of different AV delays.

One illustrative method may include monitoring electrical activity of the patient using a plurality of external electrodes disposed proximate a patient's skin during delivery of left bundle branch (LBB) pacing therapy, generating electrical heterogeneity information (EHI) based on the monitored electrical activity during delivery of left bundle branch (LBB) pacing therapy, determining a LBB pacing location for the LBB pacing therapy from a plurality of different LBB pacing locations based the EHI generated during the delivery of LBB pacing therapy at the plurality of different LBB pacing locations, and determining an atrioventricular (AV) delay for the LBB pacing therapy from a plurality of different AV delays based the EHI generated during the delivery of LBB pacing therapy at the identified LBB pacing location using the plurality of different AV delays.

One illustrative system may include an electrode apparatus comprising a plurality of external electrodes to be disposed proximate a patient's skin and a computing apparatus comprising processing circuitry and operably coupled to the electrode apparatus. The plurality of external electrodes may include a plurality of right external electrodes positioned to the right side of the patient's torso. The computing apparatus may be configured to monitor electrical activity of the patient using the plurality of external electrodes of the electrode apparatus during delivery of left bundle branch (LBB) pacing therapy and generate electrical heterogeneity information (EHI) based on the monitored electrical activity during delivery of left bundle branch (LBB) pacing therapy. The EHI may include generating a right-sided metric of dispersion of surrogate cardiac electrical activation times based on the monitored electrical activity using the plurality of right external electrodes. The computing apparatus may be further configured to determine an atrioventricular (AV) delay for the LBB pacing therapy from a plurality of different AV delays based on the EHI comprising the right-sided metric of dispersion of surrogate cardiac electrical activation times generated during the delivery of LBB pacing therapy using the plurality of different AV delays.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF ILLUSTRATIVE EMBODIMENTS

Figure 1:
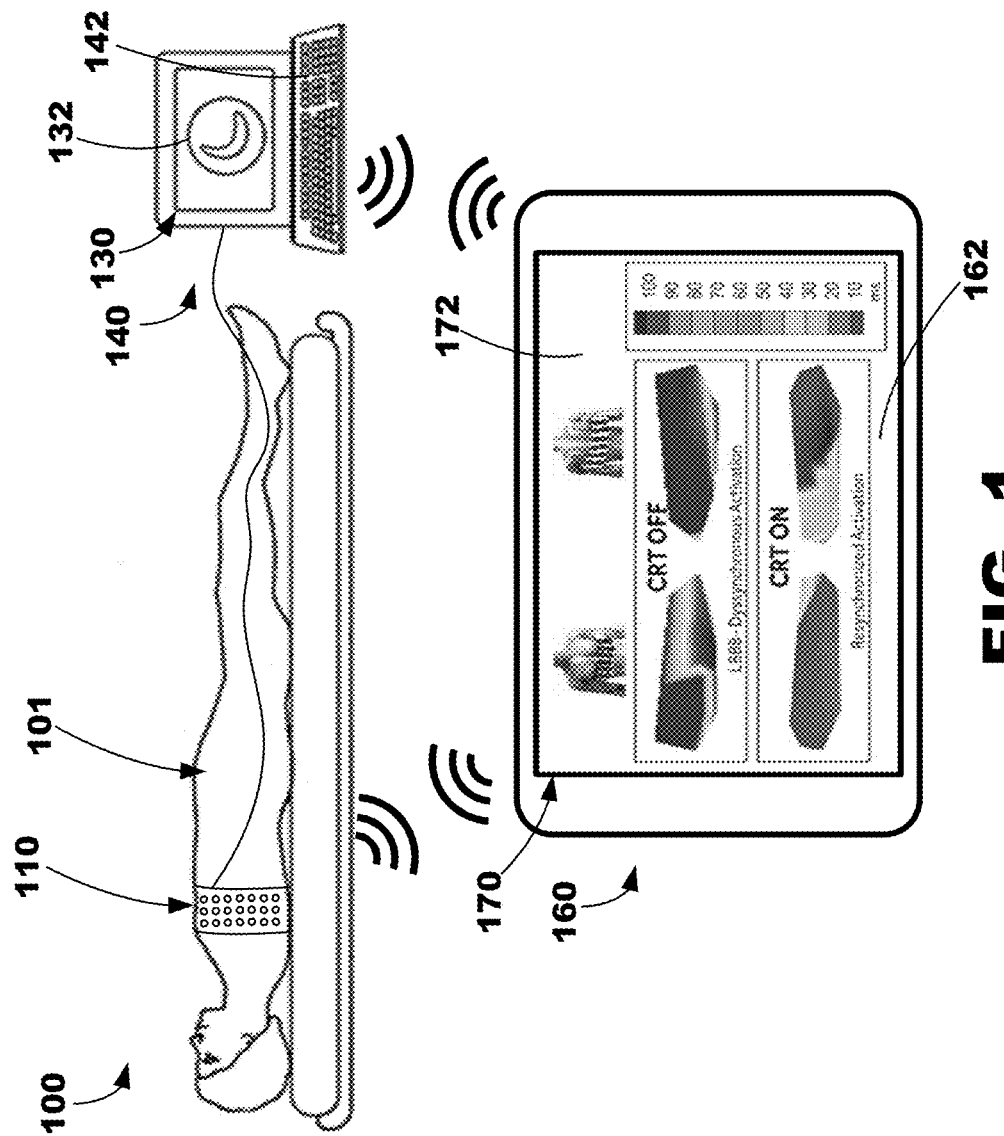
FIG. 1 is a diagram of an illustrative system including electrode apparatus, display apparatus, and computing apparatus.

In the following detailed description of illustrative embodiments, reference is made to the accompanying figures of the drawing which form a part hereof, and in which are shown, by way of illustration, specific embodiments which may be practiced. It is to be understood that other embodiments may be utilized, and structural changes may be made without departing from (e.g., still falling within) the scope of the disclosure presented hereby.

Illustrative systems and methods shall be described with reference to FIGS. 1-9. It will be apparent to one skilled in the art that elements or processes from one embodiment may be used in combination with elements or processes of the other embodiments, and that the possible embodiments of such systems and methods using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

Various illustrative systems, methods, and graphical user interfaces may be configured to use electrode apparatus including external electrodes, display apparatus, and computing apparatus to noninvasively assist a user (e.g., a physician) in the evaluation and adjust (e.g., optimize) cardiac conduction system pacing therapy, and more specifically, left bundle branch pacing therapy. An illustrative system 100 including electrode apparatus 110, computing apparatus 140, and a remote computing device 160 is depicted in FIG. 1.

The electrode apparatus 110 as shown includes a plurality of electrodes incorporated, or included, within a band wrapped around the chest, or torso, of a patient 101. The electrode apparatus 110 is operatively coupled to the computing apparatus 140 (e.g., through one or wired electrical connections, wirelessly, etc.) to provide electrical signals from each of the electrodes to the computing apparatus 140 for analysis, evaluation, etc. Illustrative electrode apparatus may be described in U.S. Pat. No. 9,320,446 entitled "Bioelectric Sensor Device and Methods" filed Mar. 27, 2014 and issued on Mar. 26, 2016, which is incorporated herein by reference in its entirety. Further, illustrative electrode apparatus 110 will be described in more detail in reference to FIGS. 2-3.

The computing apparatus 140 and the remote computing device 160 may each include display apparatus 130, 170, respectively, that may be configured to display data such as, e.g., electrical signals (e.g., electrocardiogram data), cardiac breakthrough maps, surface electrocardiographic potential maps, electrical activation times, electrical heterogeneity information, etc. For example, one cardiac cycle, or one heartbeat, of a plurality of cardiac cycles, or heartbeats, represented by the electrical signals collected or monitored by the electrode apparatus 110 may be analyzed and evaluated for one or more metrics including activation times and electrical heterogeneity information that may be pertinent to the assessment and evaluation of a patient's cardiac conduction system and/or cardiac conduction system pacing therapy delivered thereto. More specifically, for example, the QRS complex of a single cardiac cycle may be evaluated for one or more metrics such as, e.g., QRS onset, QRS offset, QRS peak, various electrical heterogeneity information (EHI) based on electrical activation times, such as left ventricular or thoracic standard deviation of electrical activation times (LVED), left ventricular dispersion, standard deviation of activation times (SDAT), average left ventricular or thoracic surrogate electrical activation times (LVAT), and referenced to earliest activation time, QRS duration (e.g., interval between QRS onset to QRS offset), difference between average left surrogate and average right surrogate activation times, relative or absolute QRS morphology, differences between a higher percentile and a lower percentile of activation times (higher percentile may be 90%, 80%, 75%, 70%, etc. and lower percentile may be 10%, 15%, 20%, 25% and 30%, etc.), other statistical measures of central tendency (e.g., median or mode), dispersion (e.g., mean deviation, standard deviation, variance, interquartile deviations, range), etc. Further, each of the one or more metrics may be location specific. For example, some metrics may be computed from signals recorded, or monitored, from electrodes positioned about a selected area of the patient such as, e.g., the left side of the patient, the right side of the patient, etc.

In at least one embodiment, one or both of the computing apparatus 140 and the remote computing device 160 may be a server, a personal computer, or a tablet computer. The computing apparatus 140 may be configured to receive input from input apparatus 142 (e.g., a keyboard) and transmit output to the display apparatus 130, and the remote computing device 160 may be configured to receive input from input apparatus 162 (e.g., a touchscreen) and transmit output to the display apparatus 170. One or both of the computing apparatus 140 and the remote computing device 160 may include data storage that may allow for access to processing programs or routines and/or one or more other types of data, e.g., for analyzing a plurality of electrical signals captured by the electrode apparatus 110, for determining cardiac breakthrough maps, a spatial representation of electrocardiographic potential, EHI, QRS onsets, QRS offsets, medians, modes, averages, peaks or maximum values, valleys or minimum values, electrical activation times, location of cardiac conduction system blocks along the cardiac conduction system (e.g., more proximal, more distal, etc.), whether the patient has left or right ventricular delays or blocks, whether one or more adjustments to pacing settings of cardiac therapy may provide effective therapy (e.g., provide improvement in cardiac resynchronization, provide improvement in cardiac heterogeneity, etc.), for driving a graphical user interface configured to noninvasively assist a user in configuring cardiac conduction system pacing therapy, one or more pacing parameters, or settings, related to such cardiac conduction system pacing therapy such as, e.g., pacing rate, ventricular pacing rate, A-V interval, V-V interval, pacing pulse width, pacing vector, multipoint pacing vector (e.g., left ventricular vector quad lead), pacing voltage, pacing configuration (e.g., biventricular pacing, right ventricle only pacing, left ventricle only pacing, etc.), and for arrhythmia detection and treatment, etc.

The computing apparatus 140 may be operatively coupled to the input apparatus 142 and the display apparatus 130 to, e.g., transmit data to and from each of the input apparatus 142 and the display apparatus 130, and the remote computing device 160 may be operatively coupled to the input apparatus 162 and the display apparatus 170 to, e.g., transmit data to and from each of the input apparatus 162 and the display apparatus 170. For example, the computing apparatus 140 and the remote computing device 160 may be electrically coupled to the input apparatus 142, 162 and the display apparatus 130, 170 using, e.g., analog electrical connections, digital electrical connections, wireless connections, bus-based connections, network-based connections, internet-based connections, etc. As described further herein, a user may provide input to the input apparatus 142, 162 to use the illustrative methods described herein, to view and/or select data such as electrical heterogeneity information generated by the illustrative methods described herein.

Although as depicted the input apparatus 142 is a keyboard and the input apparatus 162 is a touchscreen, it is to be understood that the input apparatus 142, 162 may include any apparatus capable of providing input to the computing apparatus 140 and the computing device 160 to perform the functionality, methods, and/or logic described herein. For example, the input apparatus 142, 162 may include a keyboard, a mouse, a trackball, a touchscreen (e.g., capacitive touchscreen, a resistive touchscreen, a multi-touch touchscreen, etc.), etc. Likewise, the display apparatus 130, 170 may include any apparatus capable of displaying information to a user, such as a graphical user interface 132, 172 including electrode status information, graphical maps of cardiac breakthrough, graphical maps of electrocardiographic potential, graphical maps of electrical activation, optimized LBB pacing locations, optimized LBB pacing settings such as atrioventricular (AV) delay, indications of location of cardiac conduction system block (e.g., proximally along the cardiac conduction system, distally along the cardiac conduction system, etc.), a plurality of signals for the external electrodes over one or more heartbeats, QRS complexes, various cardiac therapy scenario selection regions, various rankings of cardiac therapy scenarios, various pacing parameters, electrical heterogeneity information (EHI), textual instructions, graphical depictions of anatomy of a human heart, images or graphical depictions of the patient's heart, graphical depictions of locations of one or more electrodes, graphical depictions of a human torso, images or graphical depictions of the patient's torso, graphical depictions or actual images of implanted electrodes and/or leads, etc. Further, the display apparatus 130, 170 may include a liquid crystal display, an organic light-emitting diode screen, a touchscreen, a cathode ray tube display, etc.

It is to be understood that the computing apparatus 140 and the remote computing device 160 may be operatively coupled to each other in a plurality of different ways so as to perform, or execute, the functionality described herein. For example, in the embodiment depicted, the computing device 140 may be wireless operably coupled to the remote computing device 160 as depicted by the wireless signal lines emanating therebetween. Additionally, as opposed to wireless connections, one or more of the computing apparatus 140 and the remoting computing device 160 may be operably coupled through one or wired electrical connections.

The processing programs or routines stored and/or executed by the computing apparatus 140 and the remote computing device 160 may include programs or routines for computational mathematics, matrix mathematics, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing used to implement one or more illustrative methods and/or processes described herein. Data stored and/or used by the computing apparatus 140 and the remote computing device 160 may include, for example, electrical signal/waveform data from the electrode apparatus 110 (e.g., electrocardiographic potential or voltage over time, a plurality of QRS complexes, etc.), electrical activation times from the electrode apparatus 110, cardiac sound/signal/waveform data from acoustic sensors, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, electrical heterogeneity information, etc.), or any other data that may be used for executing, or performing, the one and/or more processes or methods described herein.

In one or more embodiments, the illustrative systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform the functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the illustrative systems, methods, and interfaces may be implemented using a computer readable storage medium, configured with a computer program, where the storage medium so configured causes the computer to operate in a specific and predefined manner to perform functions described herein. Further, in at least one embodiment, the illustrative systems, methods, and interfaces may be described as being implemented by logic (e.g., object code) encoded in one or more non-transitory media that includes code for execution and, when executed by a processor or processing circuitry, is operable to perform operations such as the methods, processes, and/or functionality described herein.

The computing apparatus 140 and the remote computing device 160 may be, for example, any fixed or mobile computer system (e.g., a controller, a microcontroller, a personal computer, minicomputer, tablet computer, etc.). The exact configurations of the computing apparatus 140 and the remote computing device 160 are not limiting, and essentially any device capable of providing suitable computing capabilities and control capabilities (e.g., signal analysis, mathematical functions such as medians, modes, averages, maximum value determination, minimum value determination, slope determination, minimum slope determination, maximum slope determination, graphics processing, etc.) may be used. As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by the computing apparatus 140 and the remote computing device 160 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes, or programs (e.g., the functionality provided by such systems, processes, or programs) described herein.

Figure 2:
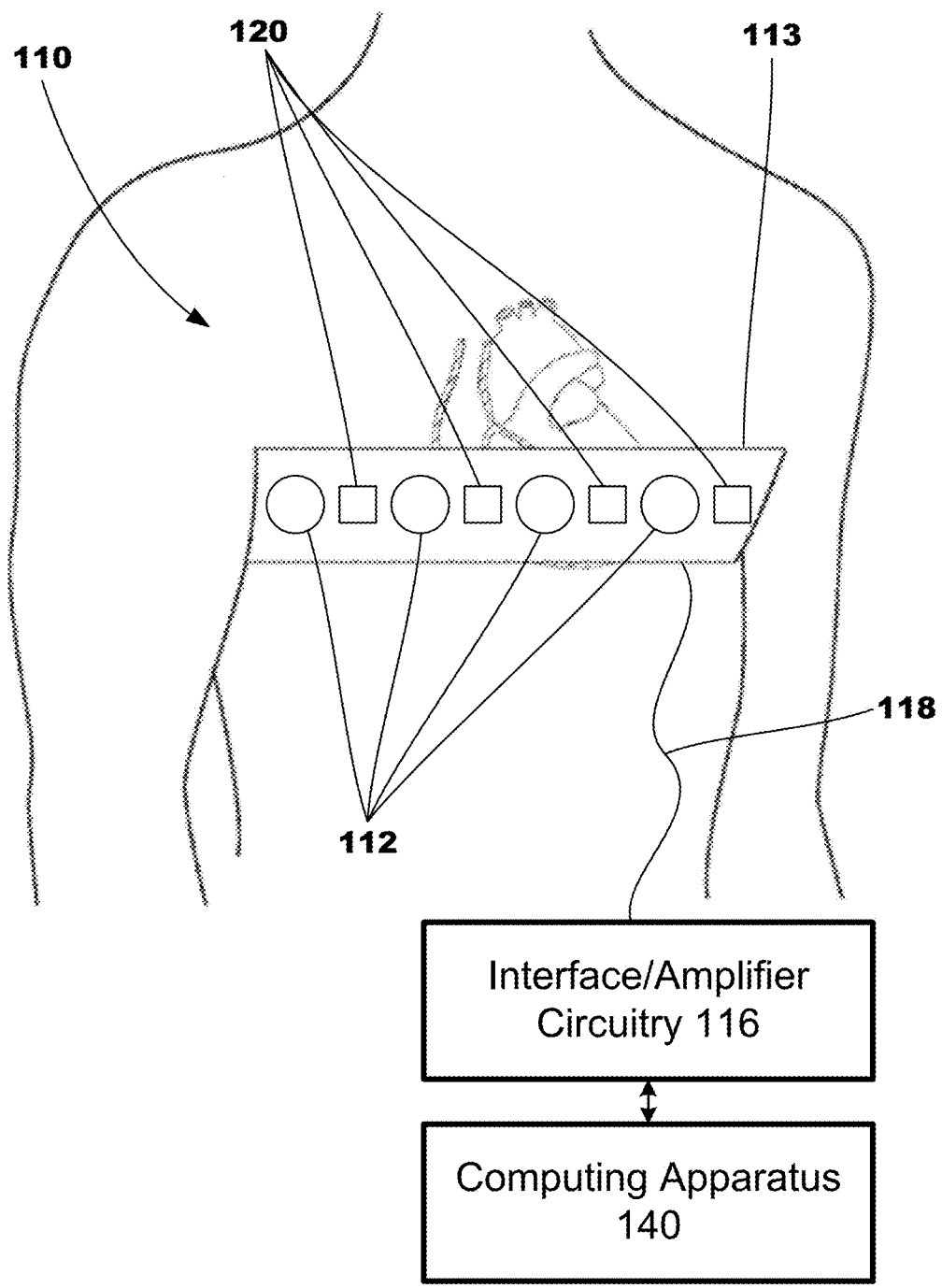
FIGS. 2-3 are diagrams of illustrative external electrode apparatus for measuring torso-surface potentials.

The illustrative electrode apparatus 110 may be configured to measure body-surface potentials of a patient 114 and, more particularly, torso-surface potentials of a patient 114. As shown in FIG. 2, the illustrative electrode apparatus 110 may include a set, or array, of external electrodes 112, a strap 113, and interface/amplifier circuitry 116. The electrodes 112 may be attached, or coupled, to the strap 113 and the strap 113 may be configured to be wrapped around the torso of a patient 114 such that the electrodes 112 surround the patient's heart. As further illustrated, the electrodes 112 may be positioned around the circumference of a patient 114, including the posterior, lateral, posterolateral, anterolateral, and anterior locations of the torso of a patient 114.

The illustrative electrode apparatus 110 may be further configured to measure, or monitor, sounds from the patient 114 (e.g., heart sounds from the torso of the patient). As shown in FIG. 2, the illustrative electrode apparatus 110 may include a set, or array, of acoustic sensors 120 attached, or coupled, to the strap 113. The strap 113 may be configured to be wrapped around the torso of a patient 114 such that the acoustic sensors 120 surround the patient's heart. As further illustrated, the acoustic sensors 120 may be positioned around the circumference of a patient 114, including the posterior, lateral, posterolateral, anterolateral, and anterior locations of the torso of a patient 114.

Further, the electrodes 112 and the acoustic sensors 120 may be electrically connected to interface/amplifier circuitry 116 via wired connection 118. The interface/amplifier circuitry 116 may be configured to amplify the signals from the electrodes 112 and the acoustic sensors 120 and provide the signals to one or both of the computing apparatus 140 and the remote computing device 160. Other illustrative systems may use a wireless connection to transmit the signals sensed by electrodes 112 and the acoustic sensors 120 to the interface/amplifier circuitry 116 and, in turn, to one or both of the computing apparatus 140 and the remote computing device 160, e.g., as channels of data. In one or more embodiments, the interface/amplifier circuitry 116 may be electrically coupled to one or both of the computing apparatus 140 and the remote computing device 160 using, e.g., analog electrical connections, digital electrical connections, wireless connections, bus-based connections, network-based connections, internet-based connections, etc.

Although in the example of FIG. 2 the electrode apparatus 110 includes a strap 113, in other examples any of a variety of mechanisms, e.g., tape or adhesives, may be employed to aid in the spacing and placement of electrodes 112 and the acoustic sensors 120. In some examples, the strap 113 may include an elastic band, strip of tape, or cloth. Further, in some examples, the strap 113 may be part of, or integrated with, a piece of clothing such as, e.g., a t-shirt. In other examples, the electrodes 112 and the acoustic sensors 120 may be placed individually on the torso of a patient 114. Further, in other examples, one or both of the electrodes 112 (e.g., arranged in an array) and the acoustic sensors 120 (e.g., also arranged in an array) may be part of, or located within, patches, vests, and/or other manners of securing the electrodes 112 and the acoustic sensors 120 to the torso of the patient 114. Still further, in other examples, one or both of the electrodes 112 and the acoustic sensors 120 may be part of, or located within, two sections of material or two patches. One of the two patches may be located on the anterior side of the torso of the patient 114 (to, e.g., monitor electrical signals representative of the anterior side of the patient's heart, measure surrogate cardiac electrical activation times representative of the anterior side of the patient's heart, monitor or measure sounds of the anterior side of the patient, etc.) and the other patch may be located on the posterior side of the torso of the patient 114 (to, e.g., monitor electrical signals representative of the posterior side of the patient's heart, measure surrogate cardiac electrical activation times representative of the posterior side of the patient's heart, monitor or measure sounds of the posterior side of the patient, etc.). And still further, in other examples, one or both of the electrodes 112 and the acoustic sensors 120 may be arranged in a top row and bottom row that extend from the anterior side of the patient 114 across the left side of the patient 114 to the posterior side of the patient 114. Yet still further, in other examples, one or both of the electrodes 112 and the acoustic sensors 120 may be arranged in a curve around the armpit area and may have an electrode/sensor-density that is less dense on the right thorax that the other remaining areas.

The electrodes 112 may be configured to surround the heart of the patient 114 and record, or monitor, the electrical signals associated with the depolarization and repolarization of the heart after the signals have propagated through the torso of a patient 114. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing.

In some examples, there may be about 12 to about 50 electrodes 112 and about 12 to about 50 acoustic sensors 120 spatially distributed around the torso of a patient. Other configurations may have more or fewer electrodes 112 and more or fewer acoustic sensors 120. It is to be understood that the electrodes 112 and acoustic sensors 120 may not be arranged or distributed in an array extending all the way around or completely around the patient 114. Instead, the electrodes 112 and acoustic sensors 120 may be arranged in an array that extends only part of the way or partially around the patient 114. For example, the electrodes 112 and acoustic sensors 120 may be distributed on the anterior, posterior, and left sides of the patient with less or no electrodes and acoustic sensors proximate the right side (including posterior and anterior regions of the right side of the patient).

One or both of the computing apparatus 140 and the remote computing device 160 may record and analyze the torso-surface potential signals sensed by electrodes 112 and the sound signals sensed by the acoustic sensors 120, which are amplified/conditioned by the interface/amplifier circuitry 116. Further, one or both of the computing apparatus 140 and the remote computing device 160 may be configured to analyze the electrical signals from the electrodes 112 to provide electrocardiogram (ECG) signals, information such as EHI, or data from the patient's heart as will be further described herein. Still further, one or both of the computing apparatus 140 and the remote computing device 160 may be configured to analyze the electrical signals from the acoustic sensors 120 to provide sound signals, information, or data from the patient's body and/or devices implanted therein (such as a left ventricular assist device).

Additionally, the computing apparatus 140 and the remote computing device 160 may be configured to provide graphical user interfaces 132, 172 depicting various information related to the electrode apparatus 110 and the data gathered, or sensed, using the electrode apparatus 110. For example, the graphical user interfaces 132, 172 may depict cardiac breakthrough maps, electrocardiographic potential maps, electrical activation maps, and EHI obtained using the electrode apparatus 110. For example, the graphical user interfaces 132, 172 may depict ECGs including QRS complexes obtained using the electrode apparatus 110 and sound data including sound waves obtained using the acoustic sensors 120 as well as other information related thereto. Illustrative systems and methods may noninvasively use the electrical information collected using the electrode apparatus 110 and the sound information collected using the acoustic sensors 120 to evaluate a patient's cardiac health and to evaluate and configure cardiac therapy being delivered to the patient. More specifically, the illustrative systems and methods may noninvasively use the electrical information collected using the electrode apparatus 110 to evaluate and adjust cardiac conduction system pacing therapy location and/or settings (e.g., LBB pacing therapy location and/or settings).

Further, the electrode apparatus 110 may further include reference electrodes and/or drive electrodes to be, e.g., positioned about the lower torso of the patient 114, that may be further used by the system 100. For example, the electrode apparatus 110 may include three reference electrodes, and the signals from the three reference electrodes may be combined to provide a reference signal. Further, the electrode apparatus 110 may use three caudal reference electrodes (e.g., instead of standard reference electrodes used in a Wilson Central Terminal) to get a "true" unipolar signal with less noise from averaging three caudally located reference signals.

Figure 3:
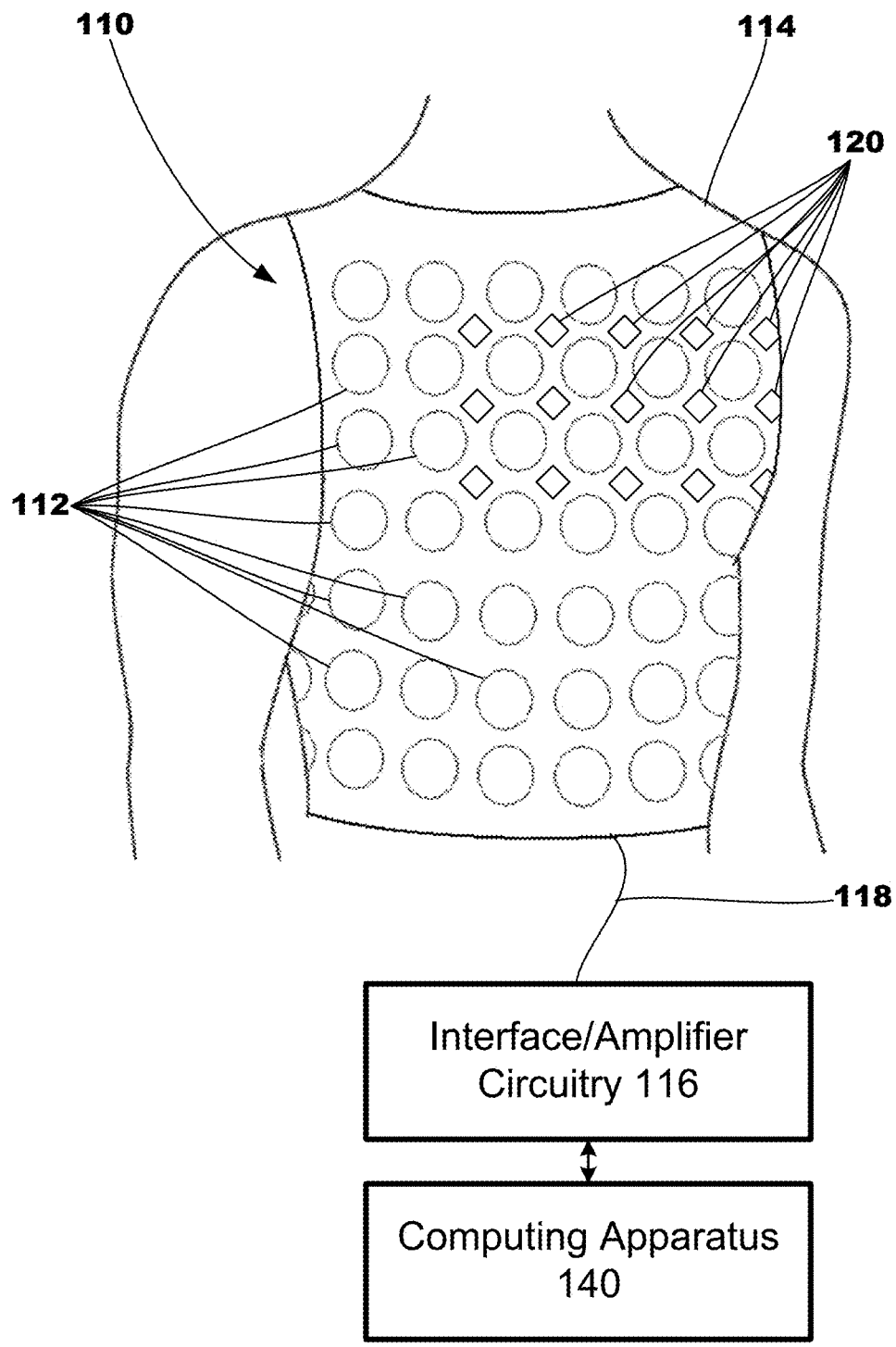

FIG. 3 illustrates another illustrative electrode apparatus 110 that includes a plurality of electrodes 112 configured to surround the heart of the patient 114 and record, or monitor, the electrical signals associated with the depolarization and repolarization of the heart after the signals have propagated through the torso of the patient 114 and a plurality of acoustic sensors 120 configured to surround the heart of the patient 114 and record, or monitor, the sound signals associated with the heart after the signals have propagated through the torso of the patient 114. The electrode apparatus 110 may include a vest 114 upon which the plurality of electrodes 112 and the plurality of acoustic sensors 120 may be attached, or to which the electrodes 112 and the acoustic sensors 120 may be coupled. In at least one embodiment, the plurality, or array, of electrodes 112 may be used to collect electrical information such as, e.g., surrogate electrical activation times. Similar to the electrode apparatus 110 of FIG.

2, the electrode apparatus 110 of FIG. 3 may include interface/amplifier circuitry 116 electrically coupled to each of the electrodes 112 and the acoustic sensors 120 through a wired connection 118 and be configured to transmit signals from the electrodes 112 and the acoustic sensors 120 to computing apparatus 140. As illustrated, the electrodes 112 and the acoustic sensors 120 may be distributed over the torso of a patient 114, including, for example, the posterior, lateral, posterolateral, anterolateral, and anterior locations of the torso of a patient 114.

The vest 114 may be formed of fabric with the electrodes 112 and the acoustic sensors 120 attached to the fabric. The vest 114 may be configured to maintain the position and spacing of electrodes 112 and the acoustic sensors 120 on the torso of the patient 114. Further, the vest 114 may be marked to assist in determining the location of the electrodes 112 and the acoustic sensors 120 on the surface of the torso of the patient 114. In some examples, there may be about 25 to about 256 electrodes 112 and about 25 to about 256 acoustic sensors 120 distributed around the torso of the patient 114, though other configurations may have more or fewer electrodes 112 and more or fewer acoustic sensors 120.

Figure 4:
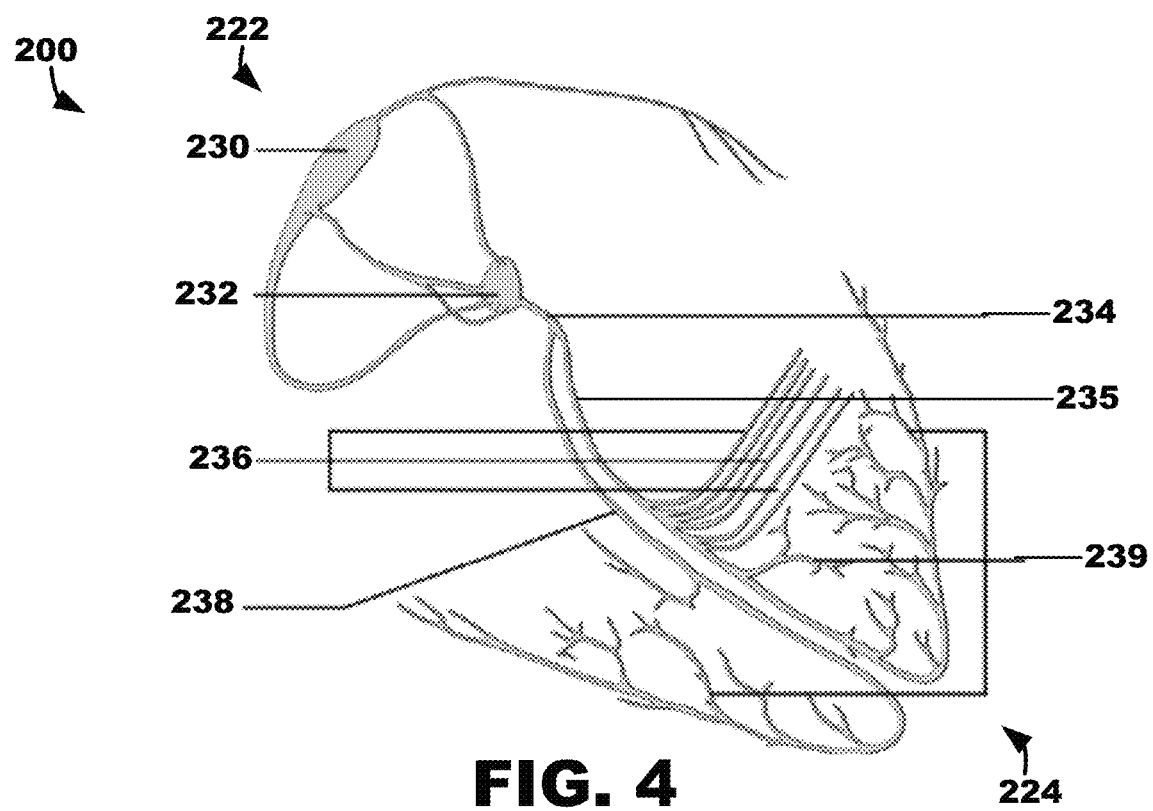
FIG. 4 depicts a patient's cardiac conduction network.

A patient's cardiac conduction network 200 is depicted in FIG. 4. As shown, the cardiac conduction network 200 extends from a proximal region 222 to a distal region 224. The cardiac conduction network 200 includes a specialized network of cells comprising the left and right bundle branches as well as a highly-branched network of specialized Purkinje fibers that aids in rapid propagation of electrical activation across the ventricles, which may lead to a very synchronized activation of the heart. The cardiac conduction system is part of the natural pathway of electrical conduction that extends from the sinoatrial node 230 to the ventricles via the atrioventricular node 232 and bundle of His 234. Further, the electrical impulses that trigger depolarization of the myocardial tissue of the patient's heart to effectively "beat" traverse the cardiac conduction network 200 from the sinoatrial node 230 to the Purkinje fibers 239.

As described herein, the proximal region 222 of the cardiac conduction network 200 may include the sinoatrial node 230 and the atrioventricular node 232 and the intermodal pathways therebetween, and the distal region 224 of the cardiac conduction network 200 may include the right bundle branch 238, the left bundle branch 235, the left posterior bundle 236, and the Purkinje fibers 239. In particular, the most distal area of the cardiac conduction network 200 may be the ends of the Purkinje fibers 239 and the most proximal area of the cardiac conduction network 200 may be the sinoatrial node 230. Thus, the cardiac conduction network 200 may be described as extending from the sinoatrial node 230 to the Purkinje fibers 239.

As noted herein, cardiac conduction system pacing therapy delivered to the left bundle branch (LBB) 235, referred to herein as LBB pacing, may be described as an attractive solution for both brady pacing therapy and cardiac resynchronization therapy (CRT) because of better thresholds, lead stability, and ease of implant compared to His bundle pacing. However, in left bundle branch block patients, LBB pacing may generate a right bundle branch block pattern of activation, which implies still delayed or later activation of the right ventricle.

It is be understood that the illustrative systems and methods described herein may be used to evaluate and adjust any type of LBB pacing such as, e.g., ventricle-from-atrium (VfA) pacing, which is further described herein with respect to FIGS. 6-9, intraseptal left ventricular endocardial pacing such as described in, for example, U.S. patent application Ser. No. 16/521,000 entitled "AV Synchronous Septal Pacing" filed on Jul. 24, 2019, which is incorporated herein by reference in its entirety, etc.

The illustrative systems and methods described herein may be used to provide noninvasive assistance to a user in the evaluation, assessment, and adjustment of cardiac conduction system pacing therapy, and in particular, the evaluation, assessment, and adjustment of LBB pacing therapy. For instance, the illustrative systems and methods may generate and use electrical heterogeneity information (EHI) based on monitored electrical activity using a plurality of noninvasive, external electrodes to determine, or identify, a LBB pacing location (e.g., an optimal LBB pacing location), and then determine, or identify, an atrioventricular (AV) delay (e.g., an optimal AV delay) for the LBB pacing.

Figure 5:
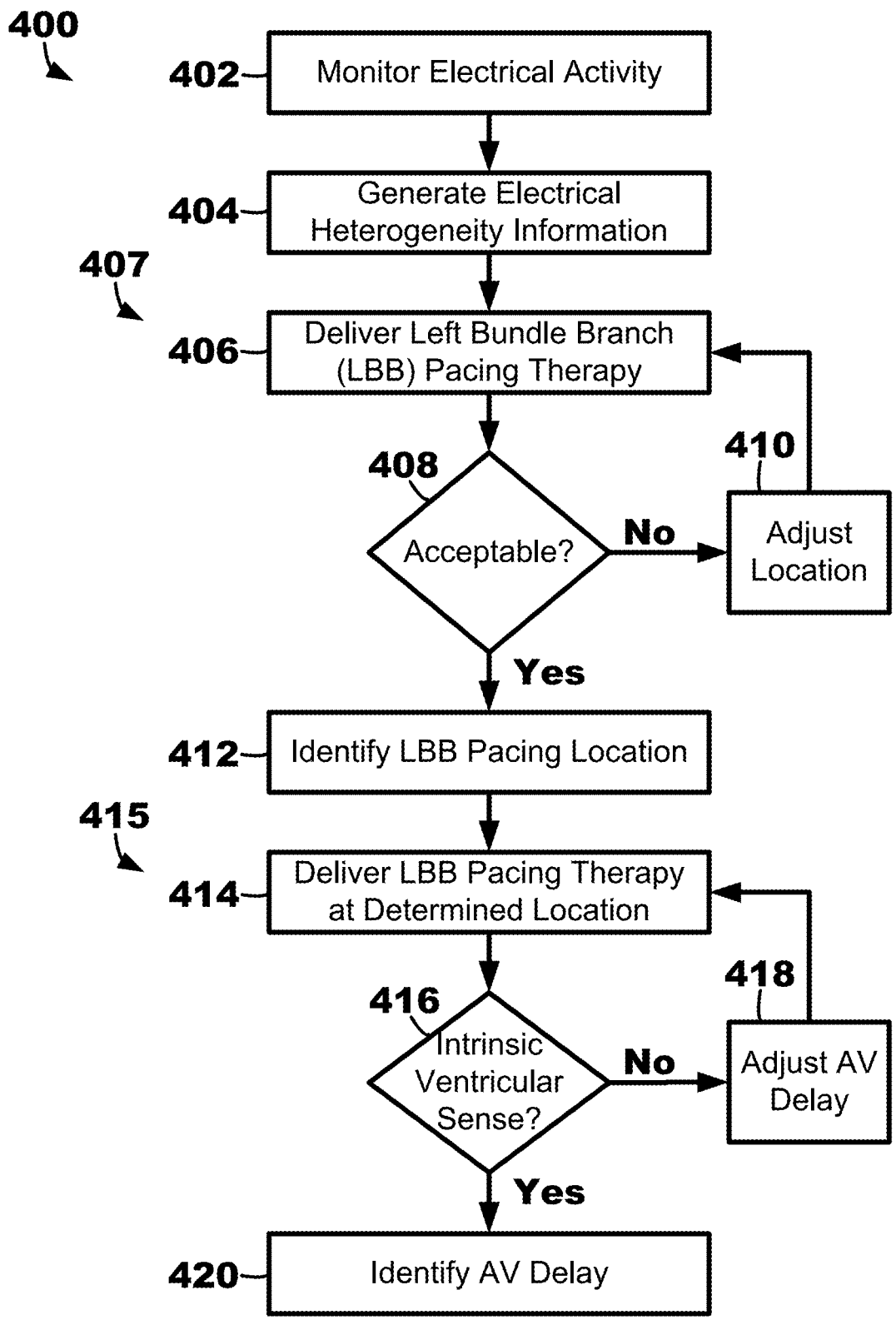
FIG. 5 is a block diagram of an illustrative method of evaluating and adjusting left bundle branch (LBB) pacing therapy.

An illustrative method 400 of evaluating, assessing, and adjusting LBB pacing therapy is depicted in FIG. 5. Generally, it may be described that the illustrative method 400 may be used to analyze external electrical activity (e.g., from the skin of the torso of the patient) during delivery of LBB pacing therapy and use such electrical activity to determine a LBB pacing location, and then analyze external electrical activity during delivery of LBB pacing therapy at the determined LBB pacing location and use such electrical activity to determine one or more settings such as AV delay for the LBB pacing therapy, each of which may assist or guide a clinician in implanting and tuning LBB pacing therapy for a patient.

The method 400 may include monitoring electrical activity 402. In one embodiment, the electrical activity may be measured externally from the patient. In other words, the electrical activity may be measured from tissue outside the patient's body (e.g., skin). For example, the method 400 may include monitoring, or measuring, electrical activity 402 using a plurality of external electrodes such as, e.g., shown and described with respect to FIGS. 1-3. In one embodiment, the plurality of external electrodes may be part, or incorporated into, a vest or band that is located about a patient's torso. More specifically, the plurality of electrodes may be described as being external surface electrodes positioned in an array configured to be located proximate the skin of the torso of a patient.

Each of the electrodes may be positioned or located about the torso of the patient so as to monitor electrical activity (e.g., acquire torso-potentials) from a plurality of different locations about the torso of the patient. Each of the different locations where the electrodes are located may correspond to the electrical activation of different portions or regions of cardiac tissue of the patient's heart. Thus, for example, the plurality of electrodes may record, or monitor, the electrical signals associated with the depolarization and repolarization of a plurality of different locations of, or about, the heart after the signals have propagated through the torso of a patient. According to various embodiments, the plurality of external electrodes may include, or comprise, a plurality of anterior electrodes that are located proximate skin of the anterior of the patient's torso, left lateral or left side electrodes that are located proximate skin of the left lateral or left side of the patient's torso, and posterior electrodes that are located proximate skin of the posterior of the patient's torso.

It may be described that, when using a plurality of external electrodes, the monitoring process 402 may provide a plurality electrocardiograms (ECGs), signals representative of the depolarization and repolarization of the patient's heart. The plurality of ECGs may, in turn, be used to generate surrogate cardiac electrical activation times representative of the depolarization of the heart. As described herein, surrogate cardiac electrical activation times may be, for example, representative of actual, or local, electrical activation times of one or more regions of the patient's heart. Measurement of activation times can be performed by picking an appropriate fiducial point (e.g., peak values, minimum values, minimum slopes, maximum slopes, zero crossings, threshold crossings, etc. of a near or far-field EGM) and measuring time between the onset of cardiac depolarization (e.g., onset of QRS complexes) and the appropriate fiducial point (e.g., within the electrical activity). The activation time between the onset of the QRS complex (or the peak Q wave) to the fiducial point may be referred to as q-LV time. In at least one embodiment, the earliest QRS onset from all of the plurality of electrodes may be utilized as the starting point for each activation time for each electrode, and the maximum slope following the onset of the QRS complex may be utilized as the end point of each activation time for each electrode.

The monitored electrical activity 402 and, in turn, the electrical activation times may be used to generate electrical heterogeneity information (EHI) 404. The EHI (e.g., data) may be defined as information indicative of at least one of mechanical synchrony or dyssynchrony of the heart and/or electrical synchrony or dyssynchrony of the heart. In other words, EHI may represent a surrogate of actual mechanical and/or electrical functionality of a patient's heart. As will be further described herein, relative changes in EHI (e.g., from initial LBB pacing location to final LBB pacing location, from an initial AV delay to a final or optimized AV delay, etc.) may be used to determine a surrogate value representative of the changes in hemodynamic response (e.g., acute changes in LV pressure gradients). Left ventricular pressure may be typically monitored invasively with a pressure sensor located in the left ventricular of a patient's heart. As such, the use of EHI to determine a surrogate value representative of the left ventricular pressure may avoid invasive monitoring using a left ventricular pressure sensor.

In at least one embodiment, the EHI may include one or more metrics of dispersion of surrogate cardiac electrical activation times such as, for example, a standard deviation of activation times (SDAT) measured using some or all of the external electrodes, e.g., of the electrode apparatus 110 described herein with respect FIGS. 1-3. Further, local, or regional, EHI may include metrics of dispersion such as standard deviations and/or averages of activation times measured using electrodes located in certain anatomic areas of the torso. For example, external electrodes on the left side of the torso of a patient may be used to compute local, or regional, left EHI.

The EHI may be generated using one or more various systems and/or methods. For example, EHI may be generated using an array, or a plurality, of surface electrodes and/or imaging systems as described in U.S. Pat. No. 9,510,763 B2 issued on Dec. 6, 2016, and entitled "ASSESSING INTRACARDIAC ACTIVATION PATTERNS AND ELECTRICAL DYSSYNCHRONY," U.S. Pat. No. 8,972,228 B2 issued Mar. 3, 2015, and entitled "ASSESSING INTRACARDIAC ACTIVATION PATTERNS", and U.S. Pat. No. 8,180,428 B2 issued May 15, 2012 and entitled "METHODS AND SYSTEMS FOR USE IN SELECTING CARDIAC PACING SITES," each of which is incorporated herein by reference in its entirety.

As described herein, EHI may include one or more metrics or indices. For example, one of the metrics, or indices, of dispersion of surrogate electrical activation times may be a standard deviation of activation times (SDAT) measured using some or all of the electrodes on the surface of the torso of a patient. In some examples, the SDAT may be calculated using the surrogate, or estimated, cardiac activation times over the surface of a model heart.

In this example, the EHI may include one or more left, or left-sided, metrics generated based on left-sided activation times of the surrogate cardiac electrical activation times measured using a plurality of left external electrodes. The left external electrodes may include a plurality of left external electrodes positioned to the left side of the patient's torso.

One left, or left-sided metric, or index, of electrical heterogeneity, or dyssynchrony, may be a left-sided metric of dispersion such as, for example, a left standard deviation of surrogate cardiac electrical activation times (LVED) monitored by external electrodes located proximate the left side of a patient. Further, another left, or left-sided metric, or index, of electrical heterogeneity may include an average of surrogate cardiac electrical activation times (LVAT) monitored by external electrodes located proximate the left side of a patient. The LVED and LVAT may be determined (e.g., calculated, computed, etc.) from electrical activity measured only by electrodes proximate the left side of the patient, which may be referred to as "left" electrodes. Activation time determined, or measured, from the left electrodes may be described as being left-sided activation times. The left electrodes may be defined as any surface electrodes located proximate the left ventricle, which includes the body or torso regions to the left of the patient's sternum and spine (e.g., toward the left arm of the patient, the left side of the patient, etc.). In one embodiment, the left electrodes may include all anterior electrodes on the left of the sternum and all posterior electrodes to the left of the spine. In another embodiment, the left electrodes may include all anterior electrodes on the left of the sternum and all posterior electrodes. In yet another embodiment, the left electrodes may be designated based on the contour of the left and right sides of the heart as determined using imaging apparatus (e.g., x-ray, fluoroscopy, etc.).

Further, in this example, the EHI may include one or more right, or right-sided, metrics generated based on right-sided activation times of the surrogate cardiac electrical activation times measured using a plurality of right external electrodes. The right external electrodes may include a plurality of right external electrodes positioned to the right side of the patient's torso.

One right, or right-sided metric, or index, of electrical heterogeneity, or dyssynchrony, may be a right-sided metric of dispersion such as, for example, a right standard deviation of surrogate cardiac electrical activation times (RVED) monitored by external electrodes located proximate the right side of a patient. Further, another right, or right-sided metric, or index, of electrical heterogeneity may include an average of surrogate cardiac electrical activation times (RVAT) monitored by external electrodes located proximate the right side of a patient. The RVED and RVAT may be determined (e.g., calculated, computed, etc.) from electrical activity measured only by electrodes proximate the right side of the patient, which may be referred to as "right" electrodes. Activation time determined, or measured, from the right electrodes may be described as being right-sided activation times. The right electrodes may be defined as any surface electrodes located proximate the right ventricle, which includes the body or torso regions to the right of the patient's sternum and spine (e.g., toward the right arm of the patient, the right side of the patient, etc.). In one embodiment, the right electrodes may include all anterior electrodes on the right of the sternum and all posterior electrodes to the right of the spine. In another embodiment, the right electrodes may include all anterior electrodes on the right of the sternum and all posterior electrodes. In yet another embodiment, the right electrodes may be designated based on the contour of the left and right sides of the heart as determined using imaging apparatus (e.g., x-ray, fluoroscopy, etc.).

Additionally, as described herein, monitoring electrical activity 402 using a plurality of external electrodes and generating EHI 404 based on the monitored electrical activity are noninvasive processes since, e.g., the external electrodes are attached to the skin of the patient as opposed to inserting or implanting any electrodes to acquire electrical activity or data. An implantable cardiac therapy device, however, may be implanted or being in the process of being finally implanted in the patient, the monitoring 402 may be performed with any cardiac therapy provided by the implantable cardiac therapy device disabled (or "turned off"). Further, it is to be understood that, although monitoring electrical activity 402 and generating EHI 404 are only depicted near the top of the diagram in FIG. 5, monitoring electrical activity 402 and generating EHI 404 occurs, or takes place, through the entire method 400. Thus, any of the remaining processes may utilize, or rely on, the electrical activity monitored and EHI generated from processes 402, 404.

The illustrative method 400 may then deliver LBB pacing therapy 406 using a cardiac conduction system pacing device. The cardiac conduction system pacing therapy may include pacing therapy that is configured to pace the LBB of the patient. For example, the LBB pacing therapy may include ventricle-from-atrium (VfA) pacing, which is further described herein with respect to FIGS. 6-9. Further, for example, the cardiac conduction system pacing therapy may include intraseptal left ventricular endocardial pacing configured to pace the LBB such as described in, for example, U.S. patent application Ser. No. 16/521,000 entitled "AV Synchronous Septal Pacing" filed on Jul. 24, 2019, which is incorporated herein by reference in its entirety.

The illustrative method 400 may then determine a LBB pacing location 407 for the LBB pacing therapy from a plurality of different LBB pacing locations during the delivery of LBB pacing therapy at the plurality of different LBB pacing locations. In at least one embodiment, determination of a LBB pacing location 407 may be based on the EHI generated during the delivery of LBB pacing therapy at the plurality of different LBB pacing locations. During determination of the LBB pacing location 407, the LBB pacing therapy may be delivered at what may be described as a "short" atrioventricular (AV) delay to avoid intrinsic ventricular activation. The AV delay is the time between an intrinsic atrial sense or pace and the delivery of the LBB pacing therapy. The short AV delay may be between about 60 milliseconds (ms) and about 120 ms. In at least one embodiment, the short AV delay may be 80 ms.

More specifically, for example, a location of the LBB pacing therapy may be evaluated and assessed to determine a LBB pacing location (e.g., an optimal LBB pacing location, an acceptable LBB pacing location, an effective LBB pacing location, etc.) in the illustrative method 400. Generally, one or more or a plurality of different LBB pacing locations may be evaluated and assessed to determine which of the different LBB pacing locations is to be identified or selected.

It is to be understood that each of a plurality of different LBB pacing locations may be provided by one or more LBB pacing electrodes positioned in a different location (e.g., moved to the different location by a clinician) than previously used and/or one or more LBB pacing electrodes being used in a LBB pacing vector different than previously used. In other words, for each different LBB pacing location, the actual location of a LBB pacing electrode may move or may not move if used in combination with other LBB pacing electrodes in a different vector.

In this embodiment, to assess and evaluate each of the plurality of different LBB pacing locations, the method 400 may analyze EHI generated from electrical activity monitored by a plurality of external electrodes during the delivering of the LBB pacing therapy for that particular pacing location. As shown, the method 400 may determine whether the LBB pacing location is acceptable (e.g., optimal, effective, best, etc.) 408.

Determination of whether the LBB pacing location is acceptable 408 may utilize one or more pieces of EHI. In at least one embodiment, the determination of whether the LBB pacing location is acceptable 408 may be based on one or metrics of dispersion of surrogate electrical activation times such as, e.g., SDAT and LVED. For example, if the SDAT is less than or equal to a SDAT threshold value, then it may be determined that the LBB pacing location is acceptable. The SDAT threshold value may be between about 10 milliseconds (ms) and about 45 ms. In at least one embodiment, the SDAT threshold value is 20 ms. Thus, if the SDAT for a particular LBB pacing location is less than or equal to 20 ms, then the LBB pacing location may be determined to be acceptable and the method 400 may identify such LBB pacing location 412. Conversely, if the SDAT for a particular LBB pacing location is not less than or equal to 20 ms, then the LBB pacing location may be determined to not be acceptable and the method 400 may adjust the pacing location 410.

Further, for example, if the LVED is less than or equal to a LVED threshold value, then it may be determined that the LBB pacing location is acceptable. The LVED threshold value may be between about 10 milliseconds (ms) and about 45 ms. In at least one embodiment, the LVED threshold value is 20 ms. Thus, if the LVED for a particular LBB pacing location is less than or equal to 20 ms, then the LBB pacing location may be determined to be acceptable and the method 400 may identify such LBB pacing location 412. Conversely, if the LVED for a particular LBB pacing location is not less than or equal to 20 ms, then the LBB pacing location may be determined to not be acceptable and the method 400 may adjust the pacing location 410.

Still further, SDAT and LVED may be used in conjunction with one another to determine whether the LBB pacing location is acceptable. For example, if the SDAT for a particular LBB pacing location is less than or equal the SDAT threshold value and the LVED for a particular LBB pacing location is less than or equal the LVED threshold value, then the LBB pacing location may be determined to be acceptable and the method 400 may identify such LBB pacing location 412. Conversely, if one of the SDAT and LVED for a particular LBB pacing location is not less than or equal to its respective threshold value, then the LBB pacing location may be determined to not be acceptable and the method 400 may adjust the pacing location 410.

It is to be understood that adjusting the pacing location 410 may be performed automatically (e.g., by changing which of the one or more LBB electrodes is being used to deliver LBB pacing therapy, by changing the vector of the LBB pacing therapy, etc.) or may be performed by a clinician upon instruction or suggest by the illustrative system and method to adjust the LBB pacing location.

After the pacing location is adjusted 410, the method 400 may continue to determine whether the new LBB pacing location is acceptable 407 by monitoring electrical activity 402, generating EHI, delivering LBB pacing 406, now at the new LBB pacing location, and evaluating whether the LBB pacing therapy is acceptable 408.

Once an acceptable (e.g., optimal) LBB pacing location has been identified, the method 400 may continue to determine one or more paced settings, such as an atrioventricular (AV) delay, for the LBB pacing therapy 415. In this embodiment an AV delay may be determined 415 from a plurality of different AV delays based the EHI generated during the delivery of LBB pacing therapy at the identified LBB pacing location 412 using the plurality of different AV delays.

Generally, to determine AV delay 415, the illustrative method 400 may start at an initial AV delay, such as the short AV delay, and adjust the AV delay by an AV delay adjustment increment until an intrinsic ventricular activation (e.g., left ventricular activation) is sensed 416 by the LBB pacing electrodes (e.g., prior to delivery of the LBB pacing pulse because the AV delay was increased beyond intrinsic activation). More specifically, the illustrative method 400 may include monitoring electrical activity 402, generating EHI 404, and delivering LBB pacing therapy at the determined LBB pacing location 414 at an AV delay and a plurality of subsequent AV delays, each different than one another until an intrinsic ventricular activations is sensed 416. The first AV delay may be the short AV delay. The AV delay increment may be tween about 5 milliseconds (ms) and about 50 ms. In at least one embodiment, the AV delay increment may be 20 ms.

If an intrinsic ventricular activation is not sensed (e.g., sensed using the LBB pacing electrodes, sensed using another sensing modality, etc.) 416, then the method 400 may adjust the AV delay 418 (e.g., increment by the AV delay increment) and continued monitoring 402, generating EHI 404, and delivering LBB pacing therapy 414 at the determined location and at the newly-adjust AV delay. If an intrinsic ventricular activation is sensed 416, then the method 400 may identify an AV delay 420 out of the one or more AV delays utilized.

To identify an AV delay out of, or from, the one or more different AV delays 420, the method 400 may evaluate one or more metrics of EHI, and in particular, one more metrics of dispersion of surrogate electrical activation times. In at least one embodiment, identification of the AV delay may be based RVED. For example, the AV delay providing the smallest, or least, RVED value may be identified 420.

Additionally, however, the AV delay providing the smallest RVED value may not provide acceptable (e.g., effective, optimal, etc.) global or left-sided metrics of dispersion of surrogate cardiac activation times. Thus, the identification of an AV delay out of, or from, the one or more different AV delays 420 may also include assessing and evaluating another, or at least one more, metric of dispersion. For example, SDAT and/or LVED may be utilized in a substantially similar ways as described herein with respect to determination 407. For example, the AV delay that provides smallest, or lowest, RVED and also maintains one or both of SDAT and LVED below their respective thresholds may be identified by process 420.

In other words, the AV delay providing the smallest, or least, RVED value, without substantially increasing at least one of SDAT or LVED during such pacing may be identified 420. A substantial increase in SDAT or LVED may be defined as a 3% increase in SDAT or LVED over the corresponding values during pacing at a "short" AV delay. Other thresholds of percentage (e.g., 1%, 2%, 4%, 5%, 6%, etc.) may be used for defining a substantial increase in SDAT or LVED.

Additionally, one or more paced parameters of the LBB pacing therapy may be also be adjusted using the illustrative systems and methods described herein such as, for example, pacing amplitude or voltage, number of pulses, pacing burst length, pacing frequency, etc. Each different parameter may be adjusted while monitoring the electrical activity 402, generating EHI 404, and analyzing such EHI, for example. Further illustrative systems, methods, and processes for optimizing the cardiac pacing therapy may be described in U.S. patent application Ser. No. 15/934,517 filed on Mar. 23, 2019 entitled "Evaluation of Ventricle from Atrium Pacing Therapy" and U.S. Prov. Pat. App. Ser. No. 62/725,763 filed on Aug. 31, 2018 entitled "Adaptive VFA Cardiac Therapy," each of which is incorporated herein by reference in its entirety.

Figure 6:
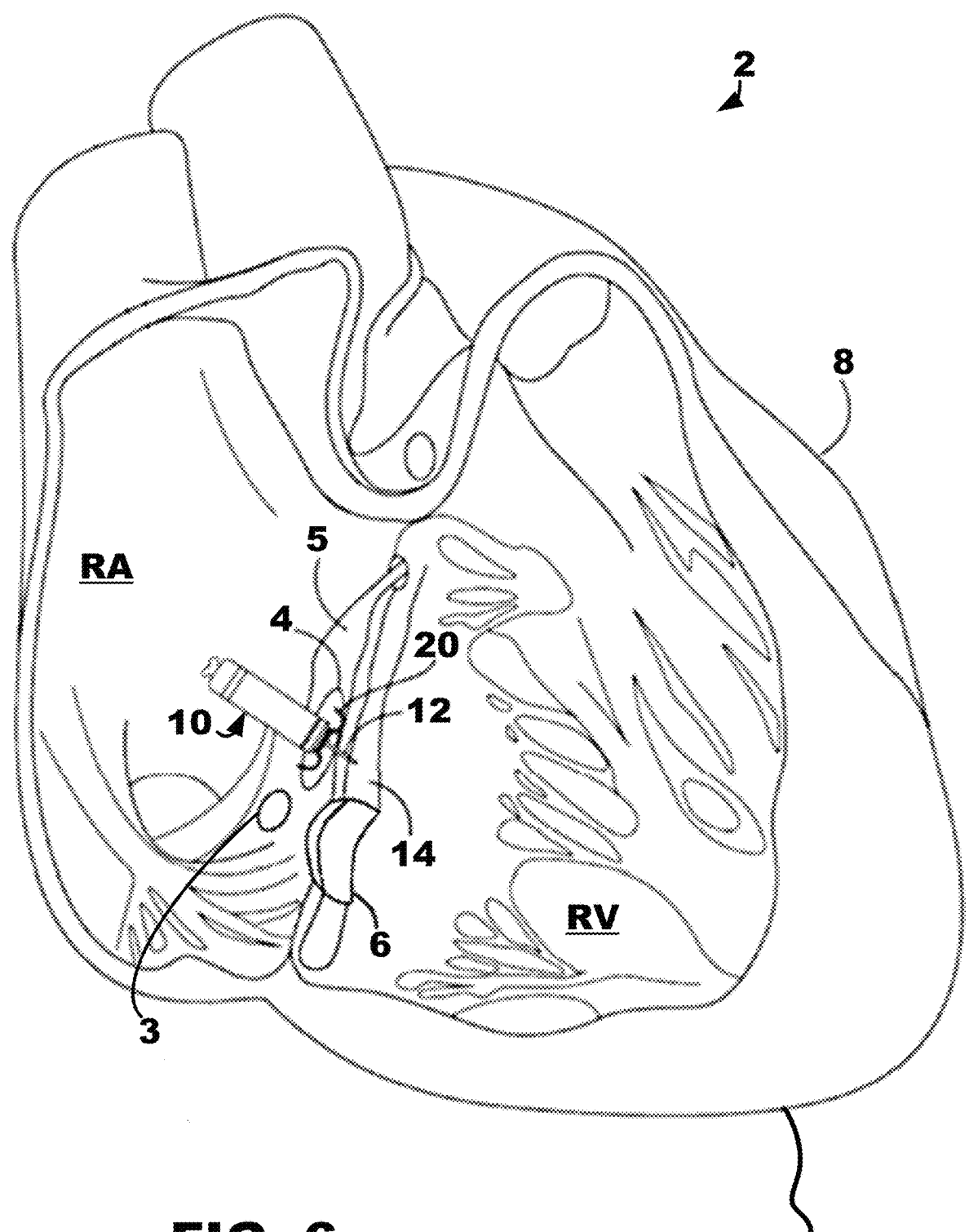
FIG. 6 is a conceptual diagram of an illustrative cardiac therapy system including an intracardiac medical device implanted in a patient's heart and a separate medical device positioned outside of the patient's heart.

An illustrative ventricle from atrium (VfA) cardiac therapy system that may be configure provide LBB pacing therapy is depicted in FIG. 6 that may be configured to be used with, for example, the systems and methods described herein with respect to FIGS. 1-5. Although it is to be understood that the present disclosure may utilize one or both of leadless and leaded implantable medical devices, the illustrative cardiac therapy system of FIG. 6 includes a leadless intracardiac medical device 10 that may be configured for single or dual chamber therapy and implanted in a patient's heart 8. In some embodiments, the device 10 may be configured for single chamber pacing and may, for example, switch between single chamber and multiple chamber pacing (e.g., dual or triple chamber pacing). As used herein, "intracardiac" refers to a device configured to be implanted entirely within a patient's heart, for example, to provide cardiac therapy. The device 10 is shown implanted in the right atrium (RA) of the patient's heart 8 in a target implant region 4. The device 10 may include one or more fixation members 20 that anchor a distal end of the device 10 against the atrial endocardium in a target implant region 4. The target implant region 4 may lie between the Bundle of His 5 and the coronary sinus 3 and may be adjacent, or next to, the tricuspid valve 6. The device 10 may be described as a ventricle-from-atrium device because, for example, the device 10 may perform, or execute, one or both of sensing electrical activity from and providing therapy to one or both ventricles (e.g., right ventricle, left ventricle, or both ventricles, depending on the circumstances) while being generally disposed in the right atrium. In particular, the device 10 may include a tissue-piercing electrode that may be implanted in the basal and/or septal region of the left ventricular myocardium of the patient's heart from the triangle of Koch region of the right atrium through the right atrial endocardium and central fibrous body.

The device 10 may be described as a leadless implantable medical device. As used herein, "leadless" refers to a device being free of a lead extending out of the patient's heart 8. Further, although a leadless device may have a lead, the lead would not extend from outside of the patient's heart to inside of the patient's heart or would not extend from inside of the patient's heart to outside of the patient's heart. Some leadless devices may be introduced through a vein, but once implanted, the device is free of, or may not include, any transvenous lead and may be configured to provide cardiac therapy without using any transvenous lead. Further, a leadless VfA device, in particular, does not use a lead to operably connect to an electrode in the ventricle when a housing of the device is positioned in the atrium. Additionally, a leadless electrode may be coupled to the housing of the medical device without using a lead between the electrode and the housing.

The device 10 may include a dart electrode assembly 12 defining, or having, a straight shaft extending from a distal end region of device 10. The dart electrode assembly 12 may be placed, or at least configured to be placed, through the atrial myocardium and the central fibrous body and into the ventricular myocardium 14, or along the ventricular septum, without perforating entirely through the ventricular endocardial or epicardial surfaces. The dart electrode assembly 12 may carry, or include, an electrode at a distal end region of the shaft such that the electrode may be positioned within the ventricular myocardium for sensing ventricular signals and delivering ventricular pacing pulses (e.g., to depolarize the left ventricle and/or right ventricle to initiate a contraction of the left ventricle and/or right ventricle). In some examples, the electrode at the distal end region of the shaft is a cathode electrode provided for use in a bipolar electrode pair for pacing and sensing. While the implant region 4 as illustrated may enable one or more electrodes of the dart electrode assembly 12 to be positioned in the ventricular myocardium, it is recognized that a device having the aspects disclosed herein may be implanted at other locations for multiple chamber pacing (e.g., dual or triple chamber pacing), single chamber pacing with multiple chamber sensing, single chamber pacing and/or sensing, or other clinical therapy and applications as appropriate.

It is to be understood that although device 10 is described herein as including a single dart electrode assembly, the device 10 may include more than one dart electrode assembly placed, or configured to be placed, through the atrial myocardium and the central fibrous body, and into the ventricular myocardium 14, or along the ventricular septum, without perforating entirely through the ventricular endocardial or epicardial surfaces. Additionally, each dart electrode assembly may carry, or include, more than a single electrode at the distal end region, or along other regions (e.g., proximal or central regions), of the shaft.

The cardiac therapy system 2 may also include a separate medical device 50 (depicted diagrammatically in FIG. 6), which may be positioned outside the patient's heart 8 (e.g., subcutaneously) and may be operably coupled to the patient's heart 8 to deliver cardiac therapy thereto. In one example, separate medical device 50 may be an extravascular ICD. In some embodiments, an extravascular ICD may include a defibrillation lead including, or carrying, a defibrillation electrode. A therapy vector may exist between the defibrillation electrode on the defibrillation lead and a housing electrode of the ICD. Further, one or more electrodes of the ICD may also be used for sensing electrical signals related to the patient's heart 8. The ICD may be configured to deliver shock therapy including one or more defibrillation or cardioversion shocks. For example, if an arrhythmia is sensed, the ICD may send a pulse via the electrical lead wires to shock the heart and restore its normal rhythm. In some examples, the ICD may deliver shock therapy without placing electrical lead wires within the heart or attaching electrical wires directly to the heart (subcutaneous ICDs). Examples of extravascular, subcutaneous ICDs that may be used with the system 2 described herein may be described in U.S. Pat. No. 9,278,229 (Reinke et al.), issued 8 Mar. 2016, which is incorporated herein by reference in its entirety.

In the case of shock therapy (e.g., defibrillation shocks provided by the defibrillation electrode of the defibrillation lead), the separate medical device 50 (e.g., extravascular ICD) may include a control circuit that uses a therapy delivery circuit to generate defibrillation shocks having any of a number of waveform properties, including leading-edge voltage, tilt, delivered energy, pulse phases, and the like. The therapy delivery circuit may, for instance, generate monophasic, biphasic, or multiphasic waveforms. Additionally, the therapy delivery circuit may generate defibrillation waveforms having different amounts of energy. For example, the therapy delivery circuit may generate defibrillation waveforms that deliver a total of between approximately 60-80 Joules (J) of energy for subcutaneous defibrillation.

The separate medical device 50 may further include a sensing circuit. The sensing circuit may be configured to obtain electrical signals sensed via one or more combinations of electrodes and to process the obtained signals. The components of the sensing circuit may include analog components, digital components, or a combination thereof. The sensing circuit may, for example, include one or more sense amplifiers, filters, rectifiers, threshold detectors, analog-to-digital converters (ADCs), or the like. The sensing circuit may convert the sensed signals to digital form and provide the digital signals to the control circuit for processing and/or analysis. For example, the sensing circuit may amplify signals from sensing electrodes and convert the amplified signals to multi-bit digital signals by an ADC, and then provide the digital signals to the control circuit. In one or more embodiments, the sensing circuit may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to the control circuit.

The device 10 and the separate medical device 50 may cooperate to provide cardiac therapy to the patient's heart 8. For example, the device 10 and the separate medical device 50 may be used to detect tachycardia, monitor tachycardia, and/or provide tachycardia-related therapy. For example, the device 10 may communicate with the separate medical device 50 wirelessly to trigger shock therapy using the separate medical device 50. As used herein, "wirelessly" refers to an operative coupling or connection without using a metal conductor between the device 10 and the separate medical device 50. In one example, wireless communication may use a distinctive, signaling, or triggering electrical pulse provided by the device 10 that conducts through the patient's tissue and is detectable by the separate medical device 50. In another example, wireless communication may use a communication interface (e.g., an antenna) of the device 10 to provide electromagnetic radiation that propagates through patient's tissue and is detectable, for example, using a communication interface (e.g., an antenna) of the separate medical device 50.

Figure 7:
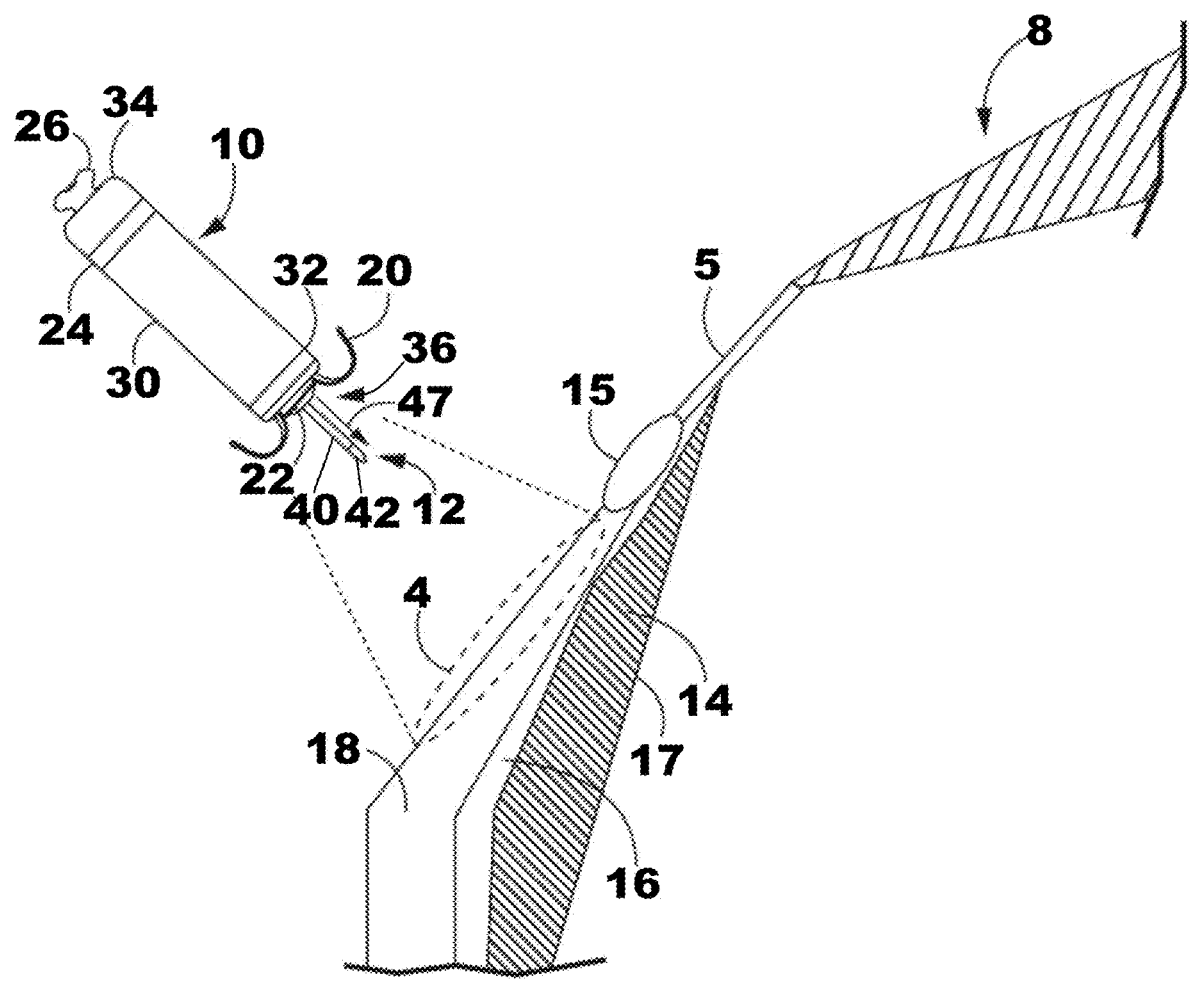
FIG. 7 is an enlarged conceptual diagram of the intracardiac medical device of FIG. 6 and anatomical structures of the patient's heart.

FIG. 7 is an enlarged conceptual diagram of the intracardiac medical device 10 of FIG. 6 and anatomical structures of the patient's heart 8. In particular, the device 10 is configured to sense cardiac signals and/or deliver pacing therapy. The intracardiac device 10 may include a housing 30. The housing 30 may define a hermetically-sealed internal cavity in which internal components of the device 10 reside, such as a sensing circuit, therapy delivery circuit, control circuit, memory, telemetry circuit, other optional sensors, and a power source as generally described in conjunction with FIG. 9. The housing 30 may include (e.g., be formed of or from) an electrically conductive material such as, e.g., titanium or titanium alloy, stainless steel, MP35N (a non-magnetic nickel-cobalt-chromium-molybdenum alloy), platinum alloy, or other bio-compatible metal or metal alloy. In other examples, the housing 30 may include (e.g., be formed of or from) a non-conductive material including ceramic, glass, sapphire, silicone, polyurethane, epoxy, acetyl co-polymer plastics, polyether ether ketone (PEEK), a liquid crystal polymer, or other biocompatible polymer.

In at least one embodiment, the housing 30 may be described as extending between a distal end region 32 and a proximal end region 34 and as defining a generally-cylindrical shape, e.g., to facilitate catheter delivery. In other embodiments, the housing 30 may be prismatic or any other shape to perform the functionality and utility described herein. The housing 30 may include a delivery tool interface member 26, e.g., defined, or positioned, at the proximal end region 34, for engaging with a delivery tool during implantation of the device 10.

All or a portion of the housing 30 may function as a sensing and/or pacing electrode during cardiac therapy. In the example shown, the housing 30 includes a proximal housing-based electrode 24 that circumscribes a proximal portion (e.g., closer to the proximal end region 34 than the distal end region 32) of the housing 30. When the housing 30 is (e.g., defines, formed from, etc.) an electrically-conductive material, such as a titanium alloy or other examples listed above, portions of the housing 30 may be electrically insulated by a non-conductive material, such as a coating of parylene, polyurethane, silicone, epoxy, or other biocompatible polymer, leaving one or more discrete areas of conductive material exposed to form, or define, the proximal housing-based electrode 24. When the housing 30 is (e.g., defines, formed from, etc.) a non-conductive material, such as a ceramic, glass or polymer material, an electrically-conductive coating or layer, such as a titanium, platinum, stainless steel, or alloys thereof, may be applied to one or more discrete areas of the housing 30 to form, or define, the proximal housing-based electrode 24. In other examples, the proximal housing-based electrode 24 may be a component, such as a ring electrode, that is mounted or assembled onto the housing 30. The proximal housing-based electrode 24 may be electrically coupled to internal circuitry of the device 10, e.g., via the electrically-conductive housing 30 or an electrical conductor when the housing 30 is a non-conductive material.

In the example shown, the proximal housing-based electrode 24 is located nearer to the housing proximal end region 34 than the housing distal end region 32, and therefore, may be referred to as a proximal housing-based electrode 24. In other examples, however, the proximal housing-based electrode 24 may be located at other positions along the housing 30, e.g., more distal relative to the position shown.

At the distal end region 32, the device 10 may include a distal fixation and electrode assembly 36, which may include one or more fixation members 20 and one or more dart electrode assemblies 12 of equal or unequal length. In one such example as shown, a single dart electrode assembly 12 includes a shaft 40 extending distally away from the housing distal end region 32 and one or more electrode elements, such as a tip electrode 42 at or near the free, distal end region of the shaft 40. The tip electrode 42 may have a conical or hemi-spherical distal tip with a relatively narrow tip-diameter (e.g., less than about 1 millimeter (mm)) for penetrating into and through tissue layers without using a sharpened tip or needle-like tip having sharpened or beveled edges.

The dart electrode assembly 12 may be configured to pierce through one or more tissue layers to position the tip electrode 42 within a desired tissue layer such as, e.g., the ventricular myocardium. As such, the height 47, or length, of the shaft 40 may correspond to the expected pacing site depth, and the shaft 40 may have a relatively-high compressive strength along its longitudinal axis to resist bending in a lateral or radial direction when pressed against and into the implant region 4. If a second dart electrode assembly 12 is employed, its length may be unequal to the expected pacing site depth and may be configured to act as an indifferent electrode for delivering of pacing energy to and/or sensing signals from the tissue. In one embodiment, a longitudinal axial force may be applied against the tip electrode 42, e.g., by applying longitudinal pushing force to the proximal end region 34 of the housing 30, to advance the dart electrode assembly 12 into the tissue within the target implant region.

The shaft 40 may be described as longitudinally non-compressive and/or elastically deformable in lateral or radial directions when subjected to lateral or radial forces to allow temporary flexing, e.g., with tissue motion, but may return to its normally straight position when lateral forces diminish. Thus, the dart electrode assembly 12 including the shaft 40 may be described as being resilient. When the shaft 40 is not exposed to any external force, or to only a force along its longitudinal central axis, the shaft 40 may retain a straight, linear position as shown.

In other words, the shaft 40 of the dart electrode assembly 12 may be a normally straight member and may be rigid. In other embodiments, the shaft 40 may be described as being relatively stiff but still possessing limited flexibility in lateral directions. Further, the shaft 40 may be non-rigid to allow some lateral flexing with heart motion. However, in a relaxed state, when not subjected to any external forces, the shaft 40 may maintain a straight position as shown to hold the tip electrode 42 spaced apart from the housing distal end region 32 at least by a height, or length, 47 of the shaft 40.

The one or more fixation members 20 may be described as one or more "tines" having a normally curved position. The tines may be held in a distally extended position within a delivery tool. The distal tips of tines may penetrate the heart tissue to a limited depth before elastically, or resiliently, curving back proximally into the normally curved position (shown) upon release from the delivery tool. Further, the fixation members 20 may include one or more aspects described in, for example, U.S. Pat. No. 9,675,579 (Grubac et al.), issued 13 Jun. 2017, and U.S. Pat. No. 9,119,959 (Rys et al.), issued 1 Sep. 2015, each of which is incorporated herein by reference in its entirety.

In some examples, the distal fixation and electrode assembly 36 includes a distal housing-based electrode 22. In the case of using the device 10 as a pacemaker for multiple chamber pacing (e.g., dual or triple chamber pacing) and sensing, the tip electrode 42 may be used as a cathode electrode paired with the proximal housing-based electrode 24 serving as a return anode electrode. Alternatively, the distal housing-based electrode 22 may serve as a return anode electrode paired with tip electrode 42 for sensing ventricular signals and delivering ventricular pacing pulses. In other examples, the distal housing-based electrode 22 may be a cathode electrode for sensing atrial signals and delivering pacing pulses to the atrial myocardium in the target implant region 4. When the distal housing-based electrode 22 serves as an atrial cathode electrode, the proximal housing-based electrode 24 may serve as the return anode paired with the tip electrode 42 for ventricular pacing and sensing and as the return anode paired with the distal housing-based electrode 22 for atrial pacing and sensing.

As shown in this illustration, the target implant region 4 in some pacing applications is along the atrial endocardium 18, generally inferior to the AV node 15 and the His bundle 5. The dart electrode assembly 12 may at least partially define the height 47, or length, of the shaft 40 for penetrating through the atrial endocardium 18 in the target implant region 4, through the central fibrous body 16, and into the ventricular myocardium 14 without perforating through the ventricular endocardial surface 17. When the height 47, or length, of the dart electrode assembly 12 is fully advanced into the target implant region 4, the tip electrode 42 may rest within the ventricular myocardium 14, and the distal housing-based electrode 22 may be positioned in intimate contact with or close proximity to the atrial endocardium 18. The dart electrode assembly 12 may have a total combined height 47, or length, of tip electrode 42 and shaft 40 from about 3 mm to about 8 mm in various examples. The diameter of the shaft 40 may be less than about 2 mm, and may be about 1 mm or less, or even about 0.6 mm or less.

Figure 8:
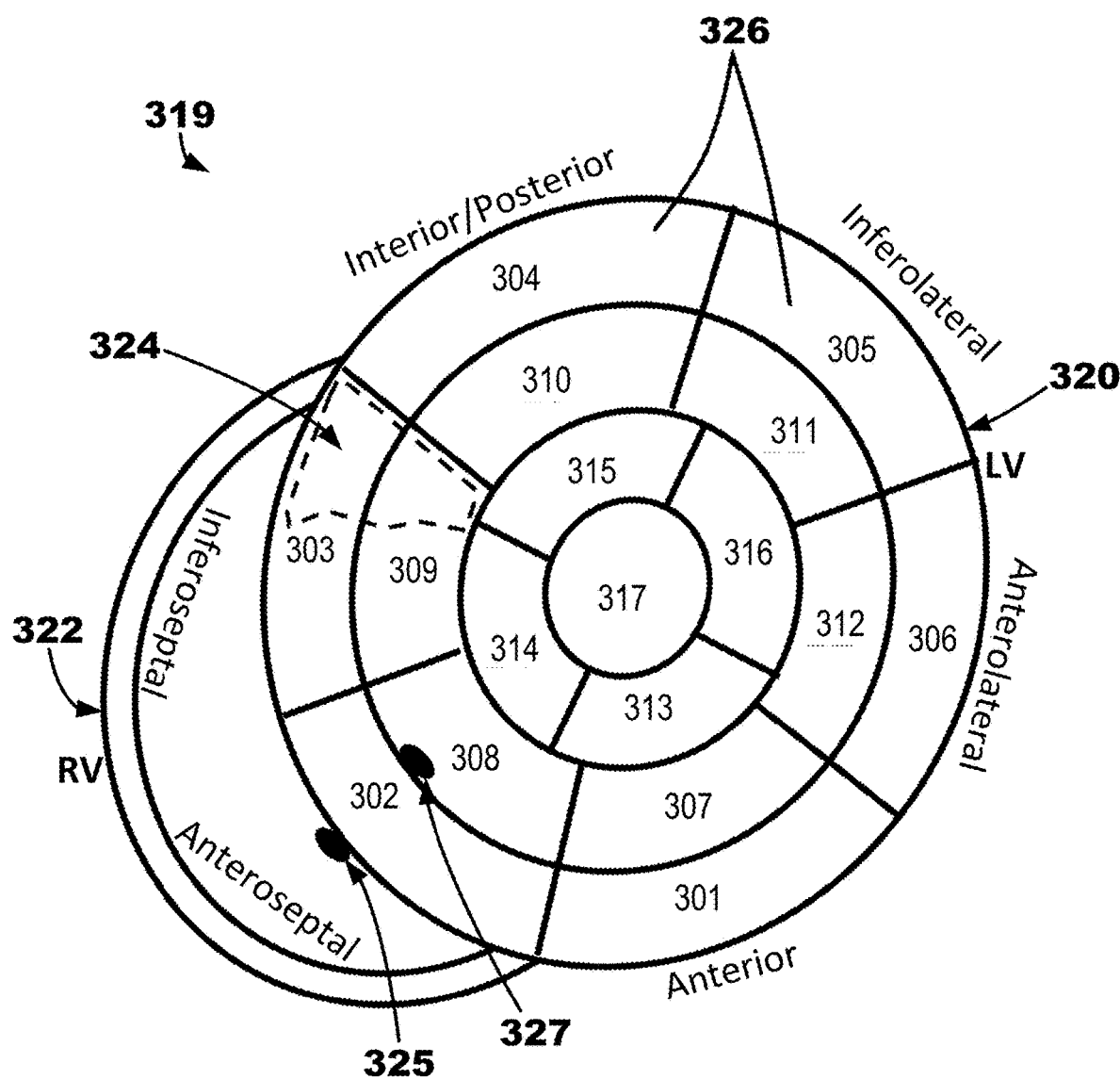
FIG. 8 is a conceptual diagram of a map of a patient's heart in a standard 17 segment view of the left ventricle showing various electrode implantation locations for use with the illustrative systems and devices described herein.

FIG. 8 is a two-dimensional (2D) ventricular map 319 of a patient's heart (e.g., a top-down view) showing the left ventricle 320 in a standard 17 segment view and the right ventricle 322. The map 319 defines, or includes, a plurality of areas 326 corresponding to different regions of a human heart. As illustrated, the areas 326 are numerically labeled 1-17 (which, e.g., correspond to a standard 17 segment model of a human heart, correspond to 17 segments of the left ventricle of a human heart, etc.). Areas 326 of the map 319 may include basal anterior area 301, basal anteroseptal area 302, basal inferoseptal area 303, basal inferior area 304, basal inferolateral area 305, basal anterolateral area 306, mid-anterior area 307, mid-anteroseptal area 308, mid-inferoseptal area 309, mid-inferior area 310, mid-inferolateral area 311, mid-anterolateral area 312, apical anterior area 313, apical septal area 314, apical inferior area 315, apical lateral area 316, and apex area 317. The inferoseptal and anteroseptal areas of the right ventricle 322 are also illustrated, as well as the right bunch branch (RBB) 325 and left bundle branch (LBB) 327.

In some embodiments, any of the tissue-piercing electrodes of the present disclosure may be implanted in the basal and/or septal region of the left ventricular myocardium of the patient's heart. In particular, the tissue-piercing electrode may be implanted from the triangle of Koch region of the right atrium through the right atrial endocardium and central fibrous body. Once implanted, the tissue-piercing electrode may be positioned in the target implant region 4 (FIGS. 6-7), such as the basal and/or septal region of the left ventricular myocardium. With reference to map 319, the basal region includes one or more of the basal anterior area 301, basal anteroseptal area 302, basal inferoseptal area 303, basal inferior area 304, mid-anterior area 307, mid-anteroseptal area 308, mid-inferoseptal area 309, and mid-inferior area 310. With reference to map 319, the septal region includes one or more of the basal anteroseptal area 302, basal anteroseptal area 303, mid-anteroseptal area 308, mid-inferoseptal area 309, and apical septal area 314.

In some embodiments, the tissue-piercing electrode may be positioned in the basal septal region of the left ventricular myocardium when implanted. The basal septal region may include one or more of the basal anteroseptal area 302, basal inferoseptal area 303, mid-anteroseptal area 308, and mid-inferoseptal area 309.

In some embodiments, the tissue-piercing electrode may be positioned in the high inferior/posterior basal septal region of the left ventricular myocardium when implanted. The high inferior/posterior basal septal region of the left ventricular myocardium may include a portion of one or more of the basal inferoseptal area 303 and mid-inferoseptal area 309 (e.g., the basal inferoseptal area only, the mid-inferoseptal area only, or both the basal inferoseptal area and the mid-inferoseptal area). For example, the high inferior/posterior basal septal region may include region 324 illustrated generally as a dashed-line boundary. As shown, the dashed line boundary represents an approximation of where the high inferior/posterior basal septal region is located, which may take a somewhat different shape or size depending on the particular application.

Figure 9:
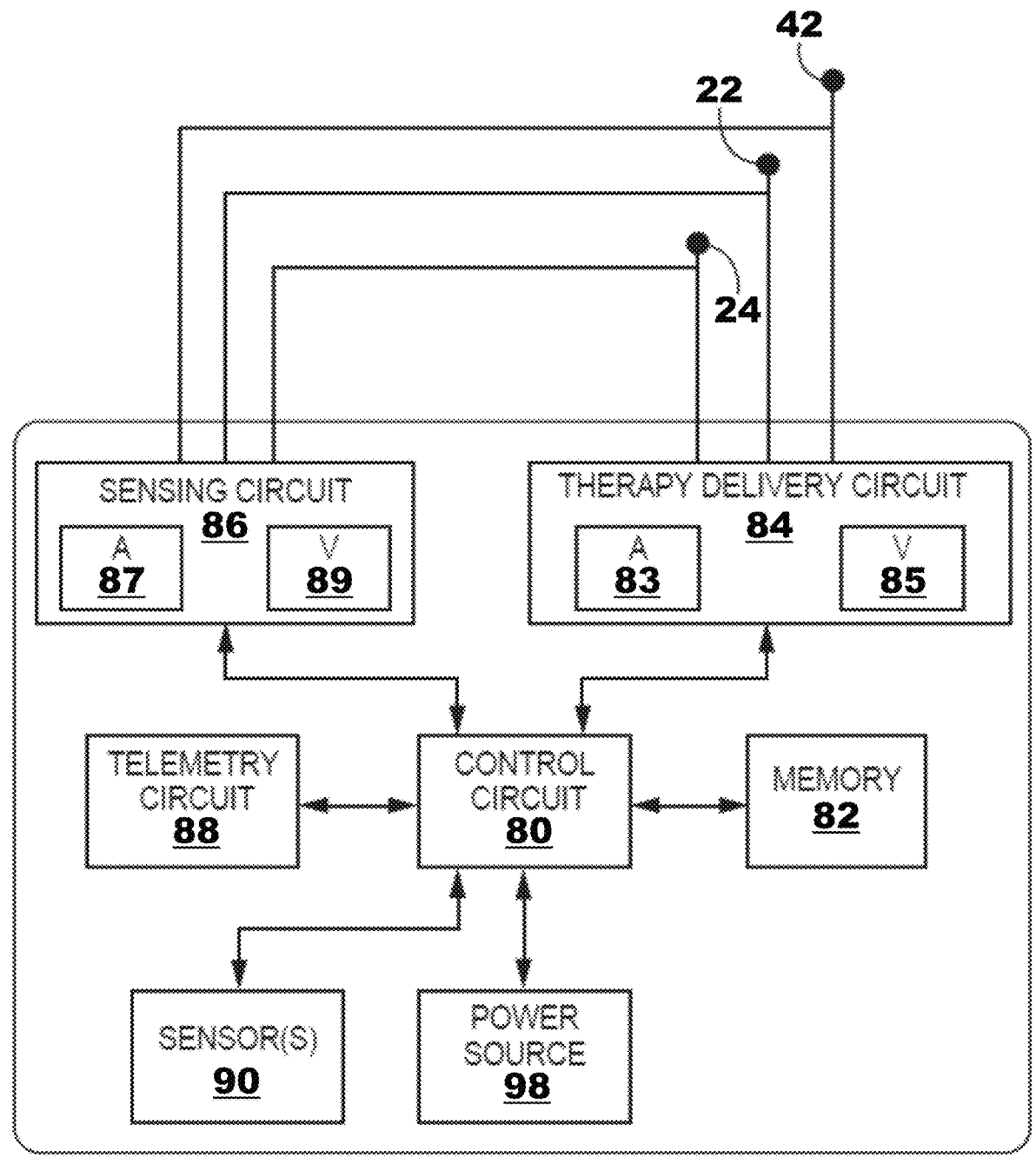
FIG. 9 is a block diagram of illustrative circuitry that may be enclosed within the housing of the medical devices of FIGS. 6-7, for example, to provide the functionality and therapy described herein.

A block diagram of circuitry is depicted in FIG. 9 that may be enclosed within the housings 30 of the device 10 to provide the functions of sensing cardiac signals, determining capture, and/or delivering pacing therapy according to one example or within the housings of any other medical devices described herein. The separate medical device 50 as shown in FIG. 6 may include some or all the same components, which may be configured in a similar manner. The electronic circuitry enclosed within the housing 30 may include software, firmware, and hardware that cooperatively monitor atrial and ventricular electrical cardiac signals, determine whether cardiac system capture has occurred, determine when a cardiac therapy is necessary, and/or deliver electrical pulses to the patient's heart according to programmed therapy mode and pulse control parameters. The electronic circuitry may include a control circuit 80 (e.g., including processing circuitry), a memory 82, a therapy delivery circuit 84, a sensing circuit 86, and/or a telemetry circuit 88. In some examples, the device 10 includes one or more sensors 90 for producing signals that are correlated to one or more physiological functions, states, or conditions of the patient. For example, the sensor(s) 90 may include a patient activity sensor, for use in determining a need for pacing therapy and/or controlling a pacing rate. In other words, the device 10 may include other sensors 90 for sensing signals from the patient for use in determining whether to deliver and/or controlling electrical stimulation therapies delivered by the therapy delivery circuit 84.

The power source 98 may provide power to the circuitry of the device 10 including each of the components 80, 82, 84, 86, 88, 90 as needed. The power source 98 may include one or more energy storage devices, such as one or more rechargeable or non-rechargeable batteries. The connections (not shown) between the power source 98 and each of the components 80, 82, 84, 86, 88, 90 may be understood from the general block diagram illustrated to one of ordinary skill in the art. For example, the power source 98 may be coupled to one or more charging circuits included in the therapy delivery circuit 84 for providing the power used to charge holding capacitors included in the therapy delivery circuit 84 that are discharged at appropriate times under the control of the control circuit 80 for delivering pacing pulses, e.g., according to a dual chamber pacing mode such as DDI(R). The power source 98 may also be coupled to components of the sensing circuit 86, such as sense amplifiers, analog-to-digital converters, switching circuitry, etc., sensors 90, the telemetry circuit 88, and the memory 82 to provide power to the various circuits.

The functional blocks shown in FIG. 9 represent functionality included in the device 10 and may include any discrete and/or integrated electronic circuit components that implement analog, and/or digital circuits capable of producing the functions attributed to the medical device 10 described herein. The various components may include processing circuitry, such as an application specific integrated circuit (ASIC), an electronic circuit, a processor (shared, dedicated, or group), and memory that execute one or more software or firmware programs, a combinational logic circuit, state machine, or other suitable components or combinations of components that provide the described functionality. The particular form of software, hardware, and/or firmware employed to implement the functionality disclosed herein will be determined primarily by the particular system architecture employed in the medical device and by the particular detection and therapy delivery methodologies employed by the medical device.

The memory 82 may include any volatile, non-volatile, magnetic, or electrical non-transitory computer readable storage media, such as random-access memory (RAM), read-only memory (ROM), non-volatile RAM (NVRAM), electrically-erasable programmable ROM (EEPROM), flash memory, or any other memory device. Furthermore, the memory 82 may include a non-transitory computer readable media storing instructions that, when executed by one or more processing circuits, cause the control circuit 80 and/or other processing circuitry to determine left bundle branch engagement and/or perform a single, dual, or triple chamber calibrated pacing therapy (e.g., single or multiple chamber pacing), or other cardiac therapy functions (e.g., sensing or delivering therapy), attributed to the device 10. The non-transitory computer-readable media storing the instructions may include any of the media listed above.

The control circuit 80 may communicate, e.g., via a data bus, with the therapy delivery circuit 84 and the sensing circuit 86 for sensing cardiac electrical signals and controlling delivery of cardiac electrical stimulation therapies in response to sensed cardiac events, e.g., P-waves and R-waves, or the absence thereof. The tip electrode 42, the distal housing-based electrode 22, and the proximal housing-based electrode 24 may be electrically coupled to the therapy delivery circuit 84 for delivering electrical stimulation pulses to the patient's heart and to the sensing circuit 86 and for sensing cardiac electrical signals.

The sensing circuit 86 may include an atrial (A) sensing channel 87 and a ventricular (V) sensing channel 89. The distal housing-based electrode 22 and the proximal housing-based electrode 24 may be coupled to the atrial sensing channel 87 for sensing atrial signals, e.g., P-waves attendant to the depolarization of the atrial myocardium. In examples that include two or more selectable distal housing-based electrodes, the sensing circuit 86 may include switching circuitry for selectively coupling one or more of the available distal housing-based electrodes to cardiac event detection circuitry included in the atrial sensing channel 87. Switching circuitry may include a switch array, switch matrix, multiplexer, or any other type of switching device suitable to selectively couple components of the sensing circuit 86 to selected electrodes. The tip electrode 42 and the proximal housing-based electrode 24 may be coupled to the ventricular sensing channel 89 for sensing ventricular signals, e.g., R-waves attendant to the depolarization of the ventricular myocardium.

Each of the atrial sensing channel 87 and the ventricular sensing channel 89 may include cardiac event detection circuitry for detecting P-waves and R-waves, respectively, from the cardiac electrical signals received by the respective sensing channels. The cardiac event detection circuitry included in each of the channels 87 and 89 may be configured to amplify, filter, digitize, and rectify the cardiac electrical signal received from the selected electrodes to improve the signal quality for detecting cardiac electrical events. The cardiac event detection circuitry within each channel 87 and 89 may include one or more sense amplifiers, filters, rectifiers, threshold detectors, comparators, analog-to-digital converters (ADCs), timers, or other analog or digital components. A cardiac event sensing threshold, e.g., a P-wave sensing threshold and an R-wave sensing threshold, may be automatically adjusted by each respective sensing channel 87 and 89 under the control of the control circuit 80, e.g., based on timing intervals and sensing threshold values determined by the control circuit 80, stored in the memory 82, and/or controlled by hardware, firmware, and/or software of the control circuit 80 and/or the sensing circuit 86.

Upon detecting a cardiac electrical event based on a sensing threshold crossing, the sensing circuit 86 may produce a sensed event signal that is passed to the control circuit 80. For example, the atrial sensing channel 87 may produce a P-wave sensed event signal in response to a P-wave sensing threshold crossing. The ventricular sensing channel 89 may produce an R-wave sensed event signal in response to an R-wave sensing threshold crossing. The sensed event signals may be used by the control circuit 80 for setting pacing escape interval timers that control the basic time intervals used for scheduling cardiac pacing pulses. A sensed event signal may trigger or inhibit a pacing pulse depending on the particular programmed pacing mode. For example, a P-wave sensed event signal received from the atrial sensing channel 87 may cause the control circuit 80 to inhibit a scheduled atrial pacing pulse and schedule a ventricular pacing pulse at a programmed atrioventricular (A-V) pacing interval. If an R-wave is sensed before the A-V pacing interval expires, the ventricular pacing pulse may be inhibited. If the A-V pacing interval expires before the control circuit 80 receives an R-wave sensed event signal from the ventricular sensing channel 89, the control circuit 80 may use the therapy delivery circuit 84 to deliver the scheduled ventricular pacing pulse synchronized to the sensed P-wave.

In some examples, the device 10 may be configured to deliver a variety of pacing therapies including bradycardia pacing, cardiac resynchronization therapy, post-shock pacing, and/or tachycardia-related therapy, such as ATP, among others. For example, the device 10 may be configured to detect non-sinus tachycardia and deliver ATP. The control circuit 80 may determine cardiac event time intervals, e.g., P-P intervals between consecutive P-wave sensed event signals received from the atrial sensing channel 87, R-R intervals between consecutive R-wave sensed event signals received from the ventricular sensing channel 89, and P-R and/or R-P intervals received between P-wave sensed event signals and R-wave sensed event signals. These intervals may be compared to tachycardia detection intervals for detecting non-sinus tachycardia. Tachycardia may be detected in a given heart chamber based on a threshold number of tachycardia detection intervals being detected.

The therapy delivery circuit 84 may include atrial pacing circuit 83 and ventricular pacing circuit 85. Each pacing circuit 83, 85 may include charging circuitry, one or more charge storage devices such as one or more low voltage holding capacitors, an output capacitor, and/or switching circuitry that controls when the holding capacitor(s) are charged and discharged across the output capacitor to deliver a pacing pulse to the pacing electrode vector coupled to respective pacing circuits 83, 85. The tip electrode 42 and the proximal housing-based electrode 24 may be coupled to the ventricular pacing circuit 85 as a bipolar cathode and anode pair for delivering ventricular pacing pulses, e.g., upon expiration of an A-V or V-V pacing interval set by the control circuit 80 for providing atrial-synchronized ventricular pacing and a basic lower ventricular pacing rate.

The atrial pacing circuit 83 may be coupled to the distal housing-based electrode 22 and the proximal housing-based electrode 24 to deliver atrial pacing pulses. The control circuit 80 may set one or more atrial pacing intervals according to a programmed lower pacing rate or a temporary lower rate set according to a rate-responsive sensor indicated pacing rate. Atrial pacing circuit may be controlled to deliver an atrial pacing pulse if the atrial pacing interval expires before a P-wave sensed event signal is received from the atrial sensing channel 87. The control circuit 80 starts an A-V pacing interval in response to a delivered atrial pacing pulse to provide synchronized multiple chamber pacing (e.g., dual or triple chamber pacing).

Charging of a holding capacitor of the atrial or ventricular pacing circuit 83, 85 to a programmed pacing voltage amplitude and discharging of the capacitor for a programmed pacing pulse width may be performed by the therapy delivery circuit 84 according to control signals received from the control circuit 80. For example, a pace timing circuit included in the control circuit 80 may include programmable digital counters set by a microprocessor of the control circuit 80 for controlling the basic pacing time intervals associated with various single chamber or multiple chamber pacing (e.g., dual or triple chamber pacing) modes or anti-tachycardia pacing sequences. The microprocessor of the control circuit 80 may also set the amplitude, pulse width, polarity, or other characteristics of the cardiac pacing pulses, which may be based on programmed values stored in the memory 82.

Control parameters utilized by the control circuit 80 for sensing cardiac events and controlling pacing therapy delivery may be programmed into the memory 82 via the telemetry circuit 88, which may also be described as a communication interface. The telemetry circuit 88 includes a transceiver and antenna for communicating with an external device, such as a programmer or home monitor, using radio frequency communication or other communication protocols. The control circuit 80 may use the telemetry circuit 88 to receive downlink telemetry from and send uplink telemetry to the external device. In some cases, the telemetry circuit 88 may be used to transmit and receive communication signals to/from another medical device implanted in the patient.

The techniques described in this disclosure, including those attributed to the IMD 10, device 50, the computing apparatus 140, and the computing device 160 and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by processing circuitry and/or one or more processors to support one or more aspects of the functionality described in this disclosure.

All references and publications cited herein are expressly incorporated herein by reference in their entirety for all purposes, except to the extent any aspect incorporated directly contradicts this disclosure.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality (for example, a first medical device may be operatively coupled to another medical device to transmit information in the form of data or to receive data therefrom).

Terms related to orientation, such as "top," "bottom," "side," and "end," are used to describe relative positions of components and are not meant to limit the orientation of the embodiments contemplated. For example, an embodiment described as having a "top" and "bottom" also encompasses embodiments thereof rotated in various directions unless the content clearly dictates otherwise.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like.

The term "and/or" means one or all the listed elements or a combination of at least two of the listed elements. The phrases "at least one of," "comprises at least one of," and "one or more of" followed by a list refers to any one of the items in the list and any combination of two or more items in the list.

Illustrative Examples

Example 1: A system comprising:
an electrode apparatus comprising a plurality of external electrodes to be disposed proximate a patient's skin; and
a computing apparatus comprising processing circuitry and operably coupled to the electrode apparatus, the computing apparatus configured to:
  monitor electrical activity of the patient using the plurality of external electrodes of the electrode apparatus during delivery of left bundle branch (LBB) pacing therapy,
  generate electrical heterogeneity information (EHI) based on the monitored electrical activity during delivery of left bundle branch (LBB) pacing therapy,
  determine a LBB pacing location for the LBB pacing therapy from a plurality of different LBB pacing locations based the EHI generated during the delivery of LBB pacing therapy at the plurality of different LBB pacing locations, and
  determine an atrioventricular (AV) delay for the LBB pacing therapy from a plurality of different AV delays based the EHI generated during the delivery of LBB pacing therapy at the determined LBB pacing location using the plurality of different AV delays.

Example 2: A method comprising:
monitoring electrical activity of the patient using a plurality of external electrodes disposed proximate a patient's skin during delivery of left bundle branch (LBB) pacing therapy,
generating electrical heterogeneity information (EHI) based on the monitored electrical activity during delivery of left bundle branch (LBB) pacing therapy;
determining a LBB pacing location for the LBB pacing therapy from a plurality of different LBB pacing locations based the EHI generated during the delivery of LBB pacing therapy at the plurality of different LBB pacing locations; and
determining an atrioventricular (AV) delay for the LBB pacing therapy from a plurality of different AV delays based the EHI generated during the delivery of LBB pacing therapy at the determined LBB pacing location using the plurality of different AV delays.

Example 3: The system of example 1 or the method of example 2, wherein generating EHI comprises generating a metric of dispersion of surrogate cardiac electrical activation times based on the monitored electrical activity,
  wherein determining the LBB pacing location for the LBB pacing therapy from the plurality of different LBB pacing locations comprises determining the LBB pacing location for the LBB pacing therapy from the plurality of different LBB pacing locations based on the metric of dispersion of surrogate cardiac electrical activation times for each the plurality of different LBB pacing locations.

Example 4: The system or method of example 3, wherein the metric of dispersion of surrogate cardiac electrical activation times is a standard deviation of surrogate cardiac electrical activation times (SDAT) based on the monitored electrical activity using the plurality of external electrodes,
  wherein determining the LBB pacing location for the LBB pacing therapy from the plurality of different LBB pacing locations comprises determining at least one LBB pacing location for the LBB pacing therapy from the plurality of different LBB pacing locations having a SDAT less than or equal to a SDAT threshold value.

Example 5: The system or method of example 4, wherein the SDAT threshold value is 20 milliseconds (ms).

Example 6: The system or method as in any one examples 3-5, wherein the plurality of external electrodes comprise a plurality of left external electrodes positioned to the left side of the patient's torso, wherein the metric of dispersion of surrogate cardiac electrical activation times is left-sided standard deviation of surrogate cardiac electrical activation times (LVED) based on the monitored electrical activity using the plurality of left external electrodes,
  wherein determining the LBB pacing location for the LBB pacing therapy from the plurality of different LBB pacing locations comprises determining at least one LBB pacing location for the LBB pacing therapy from the plurality of different LBB pacing locations having a LVED less than or equal to a LVED threshold value.

Example 7: The system or method of example 6, wherein the LVED threshold value is 20 milliseconds (ms).

Example 8: The system or method as in any one examples 1-6, wherein the delivery of LBB pacing therapy at the plurality of different LBB pacing locations utilizes a short AV delay to avoid intrinsic ventricular activation.

Example 9: The system or method as in any one examples 1-6, wherein delivery of LBB pacing therapy at the determined LBB pacing location using the plurality of different AV delays comprises delivering LBB pacing therapy at an initial AV delay and increasing the AV delay by an increment until an intrinsic left ventricular activation is sensed.

Example 10: The system or method as in any one examples 1-9, wherein the plurality of external electrodes comprise a plurality of right external electrodes positioned to the right side of the patient's torso, wherein generating EHI comprises generating a right-sided metric of dispersion of surrogate cardiac electrical activation times based on the monitored electrical activity using the plurality of right external electrodes,
  wherein determining the AV delay for the LBB pacing therapy from the plurality of different AV delays comprises determining the AV delay for the LBB pacing therapy from the plurality of different AV delays based on the right-sided metric of dispersion of surrogate cardiac electrical activation times for each the plurality of different AV delays.

Example 11: The system or method of example 10, wherein the right-sided metric of dispersion of surrogate cardiac electrical activation times is right-sided standard deviation of surrogate cardiac electrical activation times (RVED) based on the monitored electrical activity using the plurality of right external electrodes,
    wherein determining the AV delay for the LBB pacing therapy from the plurality of different AV delays comprises determining the AV delay for the LBB pacing therapy from the plurality of different AV delays having a RVED less than or equal to a RVED threshold value.

Example 12: A system comprising:
an electrode apparatus comprising a plurality of external electrodes to be disposed proximate a patient's skin, wherein the plurality of external electrodes comprise a plurality of right external electrodes positioned to the right side of the patient's torso; and
a computing apparatus comprising processing circuitry and operably coupled to the electrode apparatus, the computing apparatus configured to:
    monitor electrical activity of the patient using the plurality of external electrodes of the electrode apparatus during delivery of left bundle branch (LBB) pacing therapy,
    generate electrical heterogeneity information (EHI) based on the monitored electrical activity during delivery of left bundle branch (LBB) pacing therapy, wherein the EHI comprises generating a right-sided metric of dispersion of surrogate cardiac electrical activation times based on the monitored electrical activity using the plurality of right external electrodes, and
    determine an atrioventricular (AV) delay for the LBB pacing therapy from a plurality of different AV delays based on the EHI comprising the right-sided metric of dispersion of surrogate cardiac electrical activation times generated during the delivery of LBB pacing therapy using the plurality of different AV delays.

Example 13: The system of example 12, wherein delivery of LBB pacing therapy using the plurality of different AV delays comprises delivering LBB pacing therapy at an initial AV delay and increasing the AV delay by an increment until an intrinsic left ventricular activation is sensed.

Example 14: The system as in any one of examples 12-13, wherein the right-sided metric of dispersion of surrogate cardiac electrical activation times is right-sided standard deviation of surrogate cardiac electrical activation times (RVED) based on the monitored electrical activity using the plurality of right external electrodes.

Example 15: The system as in any one of examples 12-14, wherein determining the AV delay for the LBB pacing therapy from the plurality of different AV delays comprises determining the AV delay for the LBB pacing therapy from the plurality of different AV delays having the smallest right-sided metric of dispersion.

Example 16: The system as in any one of examples 12-15, wherein the EHI further comprises generating another metric of dispersion of surrogate cardiac electrical activation times based on the monitored electrical activity,
    wherein determining the AV delay for the LBB pacing therapy from the plurality of different AV delays comprises determining the AV delay for the LBB pacing therapy from the plurality of different AV delays having the smallest right-sided metric of dispersion and having the another metric of dispersion less than or equal to a selected dispersion threshold.

This disclosure has been provided with reference to illustrative embodiments and examples and is not meant to be construed in a limiting sense. As described previously, one skilled in the art will recognize that other various illustrative applications may use the techniques as described herein to take advantage of the beneficial characteristics of the systems, devices, and methods described herein. Various modifications of the illustrative embodiments and examples will be apparent upon reference to this description.

What is claimed:

1. A system comprising:
an electrode apparatus comprising a plurality of external electrodes to be disposed proximate a patient's skin; and
a computing apparatus comprising processing circuitry and operably coupled to the electrode apparatus, the computing apparatus configured to:
    monitor electrical activity of the patient using the plurality of external electrodes of the electrode apparatus during delivery of left bundle branch (LBB) pacing therapy,
    generate electrical heterogeneity information (EHI) based on the monitored electrical activity during delivery of left bundle branch (LBB) pacing therapy,
    determine a LBB pacing location for the LBB pacing therapy from a plurality of different LBB pacing locations based the EHI generated during the delivery of LBB pacing therapy at the plurality of different LBB pacing locations, and
    determine an atrioventricular (AV) delay for the LBB pacing therapy from a plurality of different AV delays based the EHI generated during the delivery of LBB pacing therapy at the determined LBB pacing location using the plurality of different AV delays.

2. The system of claim 1, wherein generating EHI comprises generating a metric of dispersion of surrogate cardiac electrical activation times based on the monitored electrical activity,
    wherein determining the LBB pacing location for the LBB pacing therapy from the plurality of different LBB pacing locations comprises determining the LBB pacing location for the LBB pacing therapy from the plurality of different LBB pacing locations based on the metric of dispersion of surrogate cardiac electrical activation times for each the plurality of different LBB pacing locations.

3. The system of claim 2, wherein the metric of dispersion of surrogate cardiac electrical activation times is a standard deviation of surrogate cardiac electrical activation times (SDAT) based on the monitored electrical activity using the plurality of external electrodes,
    wherein determining the LBB pacing location for the LBB pacing therapy from the plurality of different LBB pacing locations comprises determining at least one LBB pacing location for the LBB pacing therapy from the plurality of different LBB pacing locations having a SDAT less than or equal to a SDAT threshold value.

4. The system of claim 3, wherein the SDAT threshold value is 20 milliseconds (ms).

5. The system of claim 2, wherein the plurality of external electrodes comprise a plurality of left external electrodes positioned to the left side of the patient's torso, wherein the metric of dispersion of surrogate cardiac electrical activation times is left-sided standard deviation of surrogate cardiac electrical activation times (LVED) based on the monitored electrical activity using the plurality of left external electrodes,
    wherein determining the LBB pacing location for the LBB pacing therapy from the plurality of different LBB pacing locations comprises determining at least one LBB pacing location for the LBB pacing therapy from the plurality of different LBB pacing locations having a LVED less than or equal to a LVED threshold value.

6. The system of claim 5, wherein the LVED threshold value is 20 milliseconds (ms).

7. The system of claim 1, wherein the delivery of LBB pacing therapy at the plurality of different LBB pacing locations utilizes a short AV delay to avoid intrinsic ventricular activation.

8. The system of claim 1, wherein delivery of LBB pacing therapy at the determined LBB pacing location using the plurality of different AV delays comprises delivering LBB pacing therapy at an initial AV delay and increasing the AV delay by an increment until an intrinsic left ventricular activation is sensed.

9. The system of claim 1, wherein the plurality of external electrodes comprise a plurality of right external electrodes positioned to the right side of the patient's torso, wherein generating EHI comprises generating a right-sided metric of dispersion of surrogate cardiac electrical activation times based on the monitored electrical activity using the plurality of right external electrodes,
wherein determining the AV delay for the LBB pacing therapy from the plurality of different AV delays comprises determining the AV delay for the LBB pacing therapy from the plurality of different AV delays based on the right-sided metric of dispersion of surrogate cardiac electrical activation times for each the plurality of different AV delays.

10. The system of claim 9, wherein the right-sided metric of dispersion of surrogate cardiac electrical activation times is right-sided standard deviation of surrogate cardiac electrical activation times (RVED) based on the monitored electrical activity using the plurality of right external electrodes,
wherein determining the AV delay for the LBB pacing therapy from the plurality of different AV delays comprises determining the AV delay for the LBB pacing therapy from the plurality of different AV delays having a RVED less than or equal to a RVED threshold value.

11. The system of claim 9, wherein the EHI further comprises another metric of dispersion of surrogate cardiac electrical activation times based on the monitored electrical activity,
wherein determining the AV delay for the LBB pacing therapy from the plurality of different AV delays comprises determining the AV delay for the LBB pacing therapy from the plurality of different AV delays having the smallest right-sided metric of dispersion and having the another metric of dispersion less than or equal to a selected dispersion threshold.

12. The system of claim 1, wherein the electrical activity comprises electrical activation times representative of depolarization of cardiac tissue that propagates through the torso of the patient, wherein the plurality of external electrodes comprises a plurality of surface electrodes to be located proximate skin of the patient's torso.

13. The system of claim 1, wherein the LBB pacing therapy comprises one or more of ventricle-from-atrium (VfA) pacing therapy and intraseptal left ventricular endocardial pacing.

14. A method comprising:
monitoring electrical activity of the patient using a plurality of external electrodes disposed proximate a patient's skin during delivery of left bundle branch (LBB) pacing therapy;
generating electrical heterogeneity information (EHI) based on the monitored electrical activity during delivery of left bundle branch (LBB) pacing therapy;
determining a LBB pacing location for the LBB pacing therapy from a plurality of different LBB pacing locations based the EHI generated during the delivery of LBB pacing therapy at the plurality of different LBB pacing locations; and
determining an atrioventricular (AV) delay for the LBB pacing therapy from a plurality of different AV delays based the EHI generated during the delivery of LBB pacing therapy at the determined LBB pacing location using the plurality of different AV delays.

15. The method of claim 14, wherein generating EHI comprises generating a metric of dispersion of surrogate cardiac electrical activation times based on the monitored electrical activity,
wherein determining the LBB pacing location for the LBB pacing therapy from the plurality of different LBB pacing locations comprises determining the LBB pacing location for the LBB pacing therapy from the plurality of different LBB pacing locations based on the metric of dispersion of surrogate cardiac electrical activation times for each the plurality of different LBB pacing locations.

16. The method of claim 15, wherein the metric of dispersion of surrogate cardiac electrical activation times is a standard deviation of surrogate cardiac electrical activation times (SDAT) based on the monitored electrical activity using the plurality of external electrodes,
wherein determining the LBB pacing location for the LBB pacing therapy from the plurality of different LBB pacing locations comprises determining at least one LBB pacing location for the LBB pacing therapy from the plurality of different LBB pacing locations having a SDAT less than or equal to a SDAT threshold value.

17. The method of claim 15, wherein the plurality of external electrodes comprise a plurality of left external electrodes positioned to the left side of the patient's torso, wherein the metric of dispersion of surrogate cardiac electrical activation times is left-sided standard deviation of surrogate cardiac electrical activation times (LVED) based on the monitored electrical activity using the plurality of left external electrodes,
wherein determining the LBB pacing location for the LBB pacing therapy from the plurality of different LBB pacing locations comprises determining at least one LBB pacing location for the LBB pacing therapy from the plurality of different LBB pacing locations having a LVED less than or equal to a LVED threshold value.

18. The method of claim 14, wherein the delivery of LBB pacing therapy at the plurality of different LBB pacing locations utilizes a short AV delay to avoid intrinsic ventricular activation.

19. The method of claim 14, wherein delivery of LBB pacing therapy at the determined LBB pacing location using the plurality of different AV delays comprises delivering LBB pacing therapy at an initial AV delay and increasing the AV delay by an increment until an intrinsic left ventricular activation is sensed.

20. The method of claim 14, wherein the plurality of external electrodes comprise a plurality of right external electrodes positioned to the right side of the patient's torso, wherein generating EHI comprises generating a right-sided metric of dispersion of surrogate cardiac electrical activation times based on the monitored electrical activity using the plurality of right external electrodes, wherein determining the AV delay for the LBB pacing therapy from the plurality of different AV delays comprises determining the AV delay for the LBB pacing therapy from the plurality of different AV delays based on the right-sided metric of dispersion of surrogate cardiac electrical activation times for each the plurality of different AV delays.

21. The method of claim 20, wherein the right-sided metric of dispersion of surrogate cardiac electrical activation times is right-sided standard deviation of surrogate cardiac electrical activation times (RVED) based on the monitored electrical activity using the plurality of right external electrodes,
wherein determining the AV delay for the LBB pacing therapy from the plurality of different AV delays comprises determining the AV delay for the LBB pacing therapy from the plurality of different AV delays having a RVED less than or equal to a RVED threshold value.

22. The method of claim 20, wherein the EHI further comprises another metric of dispersion of surrogate cardiac electrical activation times based on the monitored electrical activity,
wherein determining the AV delay for the LBB pacing therapy from the plurality of different AV delays comprises determining the AV delay for the LBB pacing therapy from the plurality of different AV delays having the smallest right-sided metric of dispersion and having the another metric of dispersion less than or equal to a selected dispersion threshold.

23. The method of claim 14, wherein the electrical activity comprises electrical activation times representative of depolarization of cardiac tissue that propagates through the torso of the patient, wherein the plurality of external electrodes comprises a plurality of surface electrodes to be located proximate skin of the patient's torso.

24. The method of claim 14, wherein the LBB pacing therapy comprises one or more of ventricle-from-atrium (VfA) pacing therapy and intraseptal left ventricular endocardial pacing.

25. A system comprising:
an electrode apparatus comprising a plurality of external electrodes to be disposed proximate a patient's skin, wherein the plurality of external electrodes comprise a plurality of right external electrodes positioned to the right side of the patient's torso; and
a computing apparatus comprising processing circuitry and operably coupled to the electrode apparatus, the computing apparatus configured to:
monitor electrical activity of the patient using the plurality of external electrodes of the electrode apparatus during delivery of left bundle branch (LBB) pacing therapy,
generate electrical heterogeneity information (EHI) based on the monitored electrical activity during delivery of left bundle branch (LBB) pacing therapy, wherein the EHI comprises generating a right-sided metric of dispersion of surrogate cardiac electrical activation times based on the monitored electrical activity using the plurality of right external electrodes, and
determine an atrioventricular (AV) delay for the LBB pacing therapy from a plurality of different AV delays based on the EHI comprising the right-sided metric of dispersion of surrogate cardiac electrical activation times generated during the delivery of LBB pacing therapy using the plurality of different AV delays.

26. The system of claim 25, wherein delivery of LBB pacing therapy using the plurality of different AV delays comprises delivering LBB pacing therapy at an initial AV delay and increasing the AV delay by an increment until an intrinsic left ventricular activation is sensed.

27. The system of claim 25, wherein the right-sided metric of dispersion of surrogate cardiac electrical activation times is right-sided standard deviation of surrogate cardiac electrical activation times (RVED) based on the monitored electrical activity using the plurality of right external electrodes.

28. The system of claim 25, wherein determining the AV delay for the LBB pacing therapy from the plurality of different AV delays comprises determining the AV delay for the LBB pacing therapy from the plurality of different AV delays having the smallest right-sided metric of dispersion.

29. The system of claim 25, wherein the EHI further comprises generating another metric of dispersion of surrogate cardiac electrical activation times based on the monitored electrical activity,
wherein determining the AV delay for the LBB pacing therapy from the plurality of different AV delays comprises determining the AV delay for the LBB pacing therapy from the plurality of different AV delays having the smallest right-sided metric of dispersion and having the another metric of dispersion less than or equal to a selected dispersion threshold.

* * * * *